United States Patent [19]

Farone

[11] Patent Number: 5,262,961
[45] Date of Patent: Nov. 16, 1993

[54] METHOD FOR MONITORING AND CONTROLLING A CHEMICAL PROCESS

[76] Inventor: William A. Farone, 14112 Picasso Ct., Irvine, Calif. 92714

[21] Appl. No.: 628,321

[22] Filed: Dec. 17, 1990

[51] Int. Cl.$^5$ .............................. G06F 15/46
[52] U.S. Cl. ................................ 364/500
[58] Field of Search ............ 364/496, 497, 498, 499, 364/550, 554

[56] References Cited

U.S. PATENT DOCUMENTS

| | | | |
|---|---|---|---|
| 3,800,288 | 3/1974 | Russell et al. | |
| 4,267,572 | 5/1981 | Witte | 364/498 |
| 4,365,303 | 12/1982 | Hannah et al. | 364/498 |
| 4,396,977 | 8/1983 | Slater et al. | 364/500 X |
| 4,660,151 | 4/1987 | Chipman et al. | 364/498 |
| 4,692,883 | 9/1987 | Nelson et al. | 364/497 X |
| 4,855,930 | 8/1989 | Chao et al. | 364/497 |
| 5,046,846 | 9/1991 | Ray et al. | 364/498 X |
| 5,121,338 | 6/1992 | Lodder | 364/498 |
| 5,121,443 | 6/1992 | Tomlinson | 364/498 X |

OTHER PUBLICATIONS

American Laboratory; Nov. 1976; "A Microcomputer-Controlled Infrared Analyzer for Multicomponent Analysis"; pp. 91–100.

Primary Examiner—Kevin J. Teska

[57] ABSTRACT

An on-line method of monitoring and controlling a chemical process is based on measuring the concentration of process reactants and products using spectrometric technology. The spectral data is analyzed using a modified chi-squared processing method to determine the unknown concentration of reactants and products in test samples withdrawn from the process. This method avoids the need for the spectral data to conform to Beer's Law and the best spectral range is determined automatically. The physical parameters of the process are monitored and altered based on this determination as required to optimize the process.

3 Claims, 24 Drawing Sheets

.25% Fructose in Water

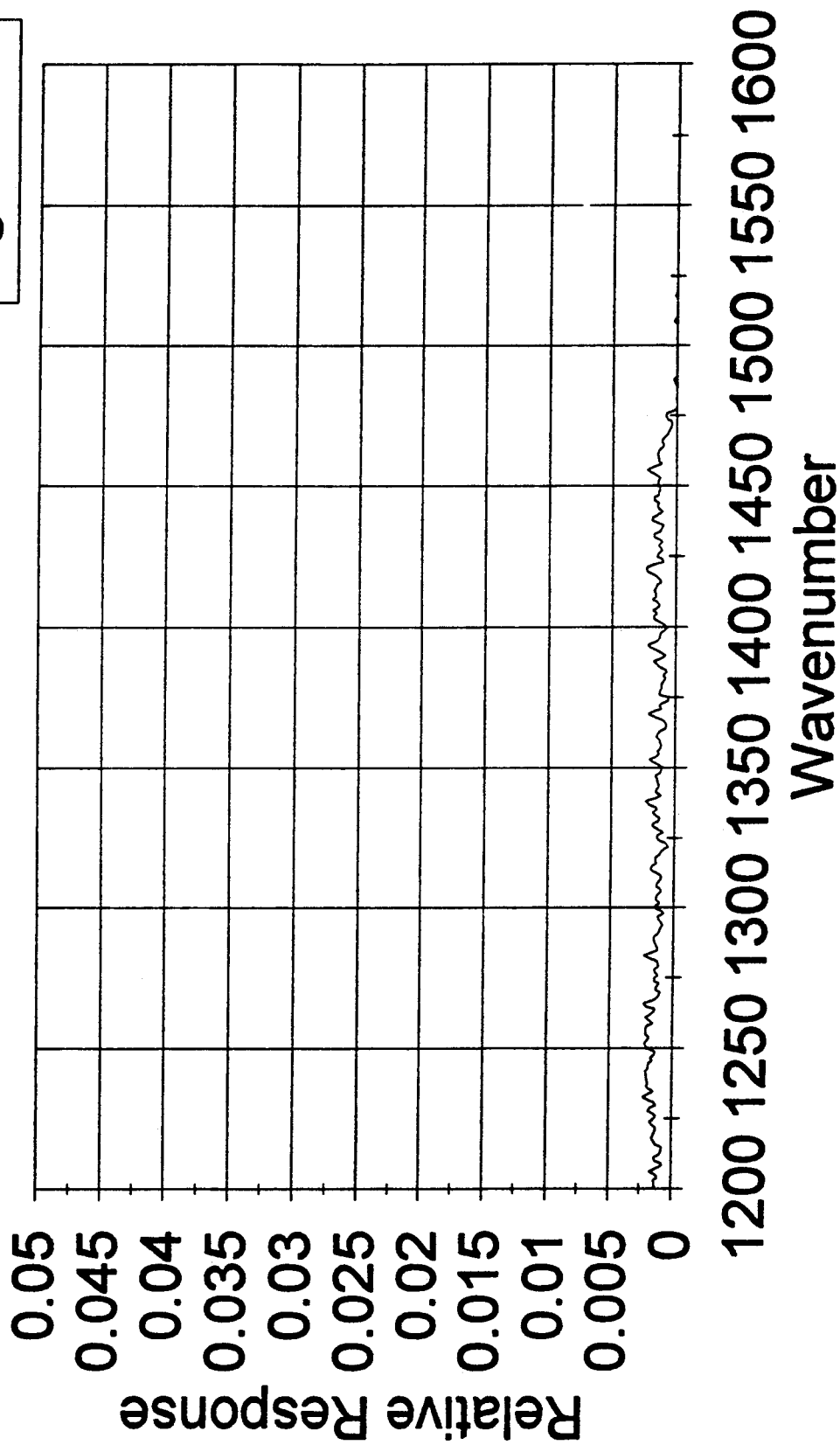
Figure 2B .25% Fructose in Water

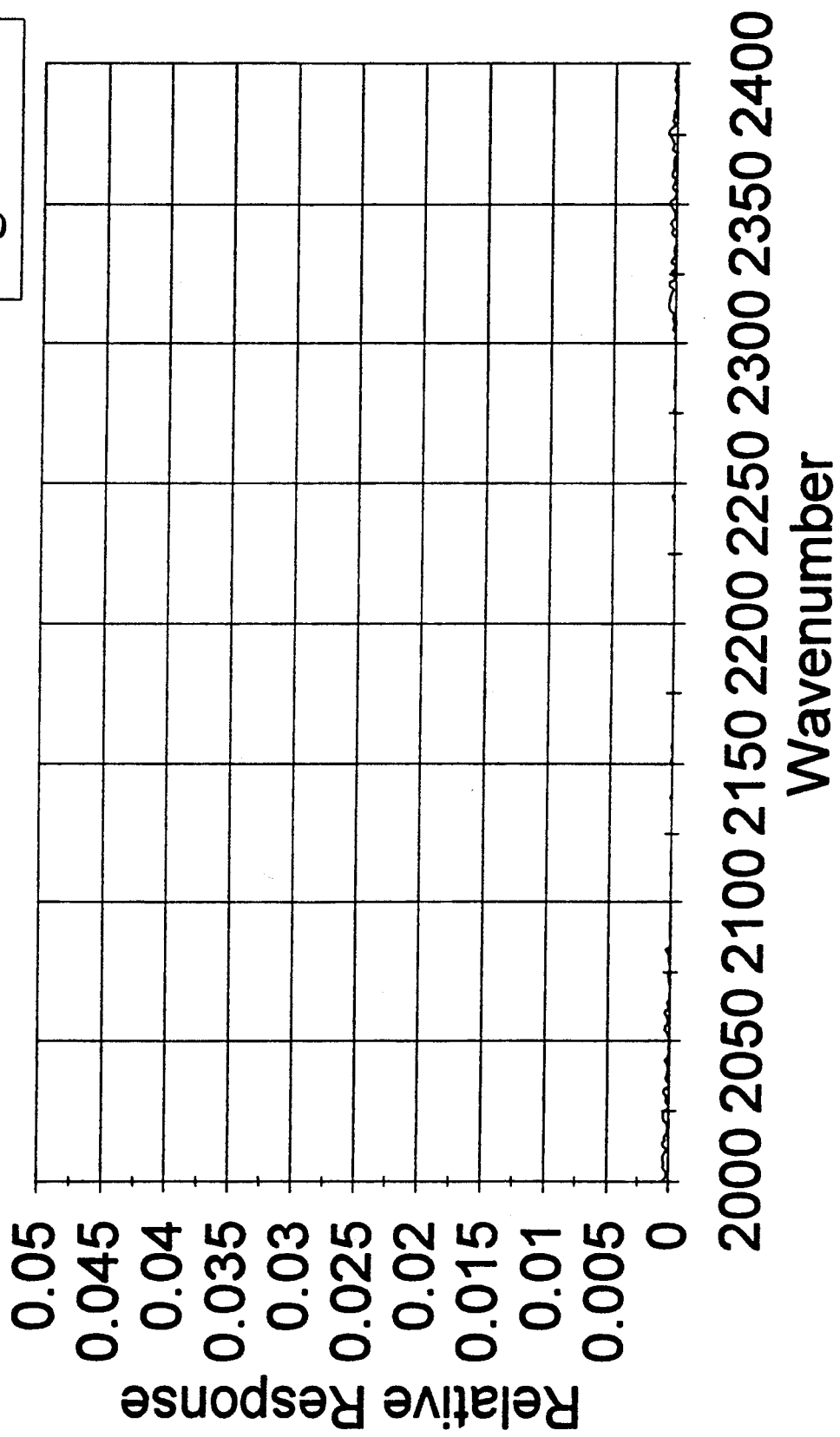

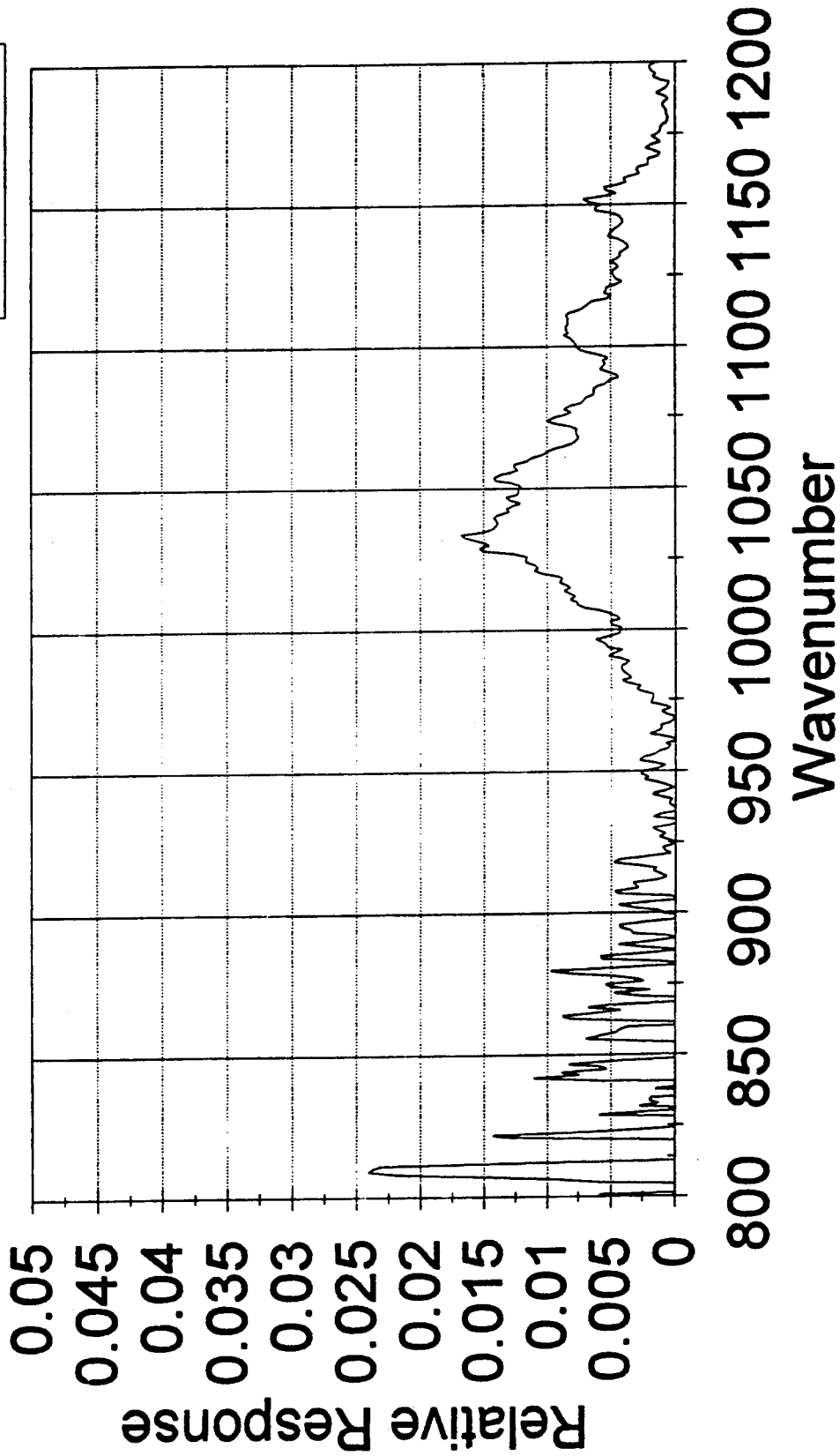

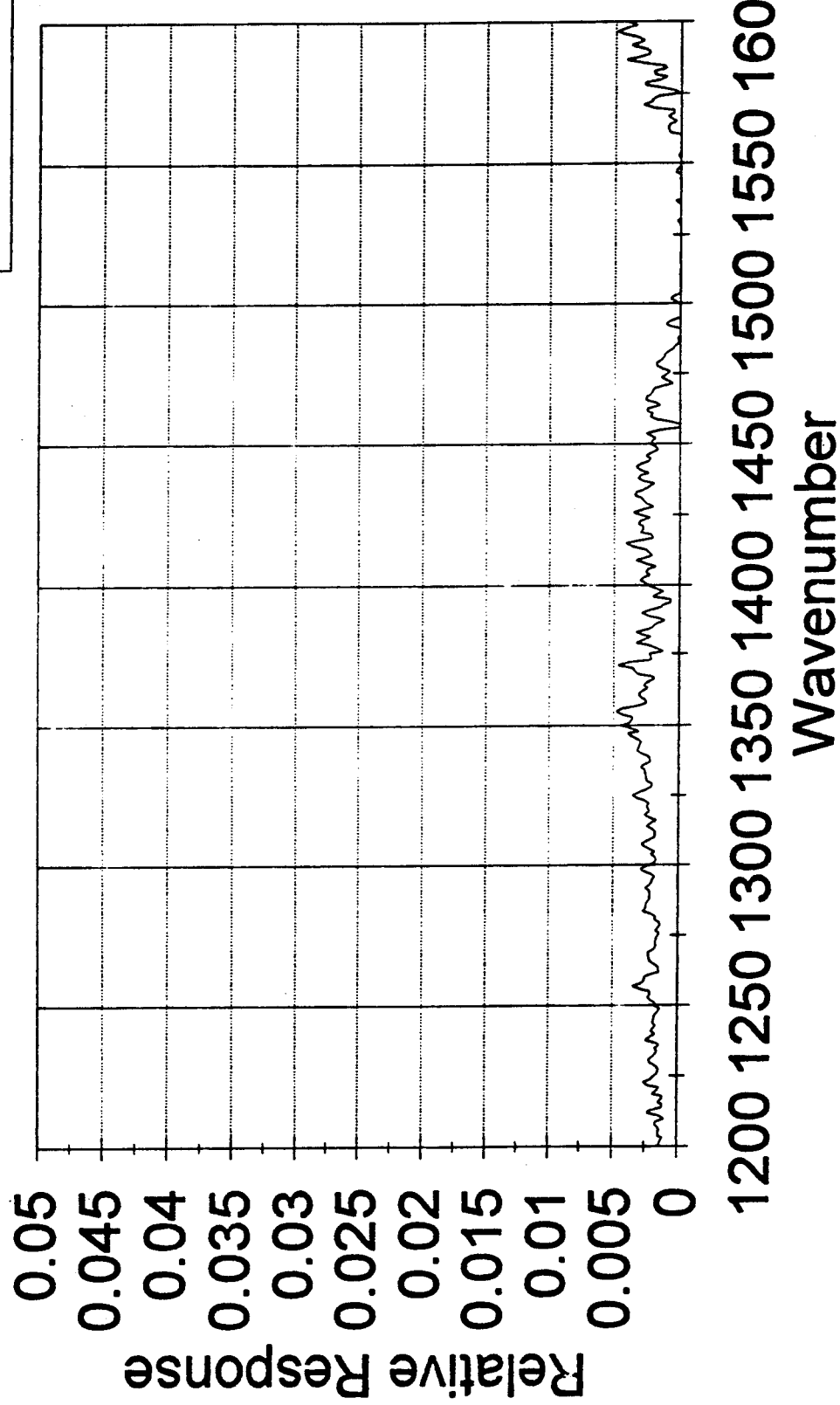

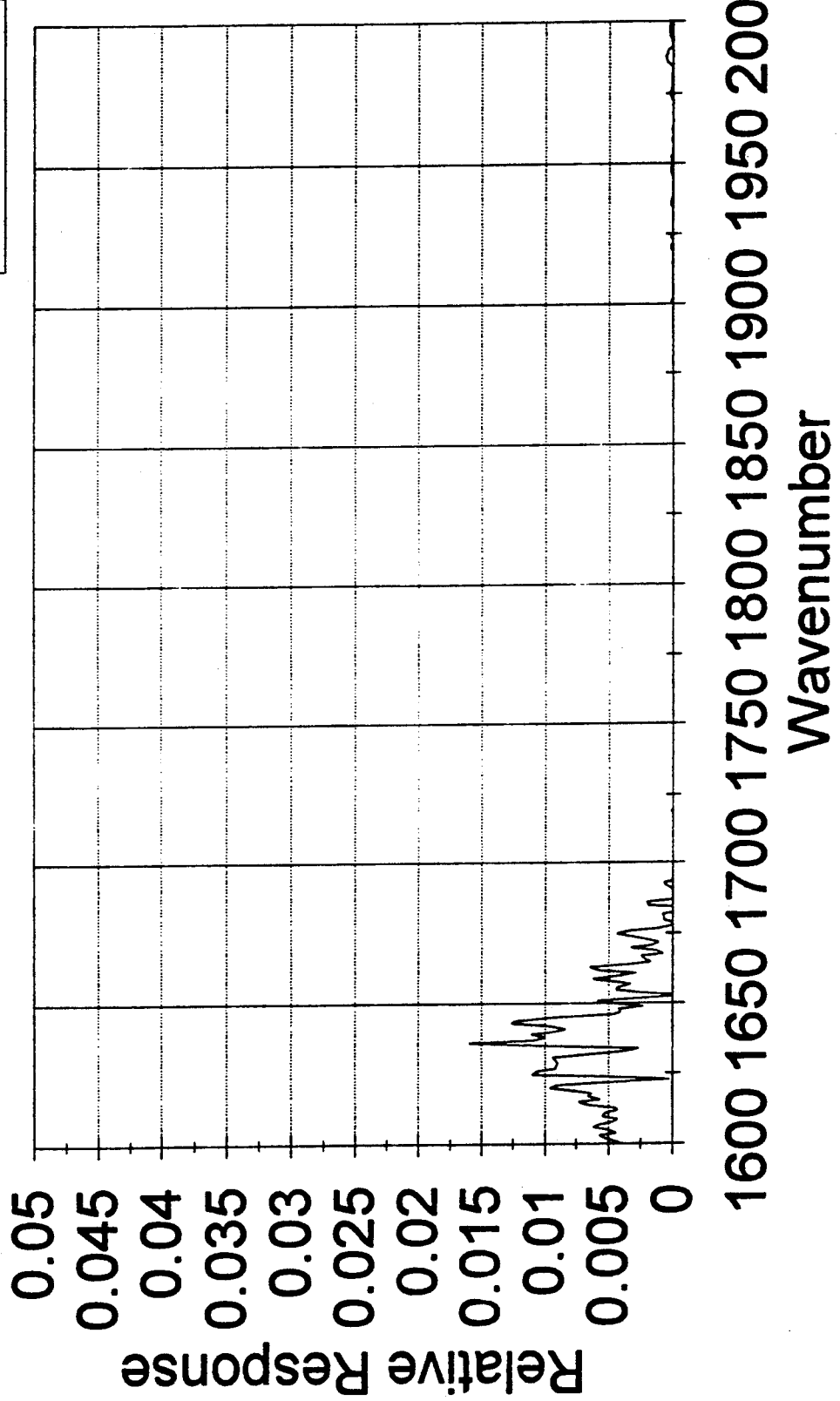

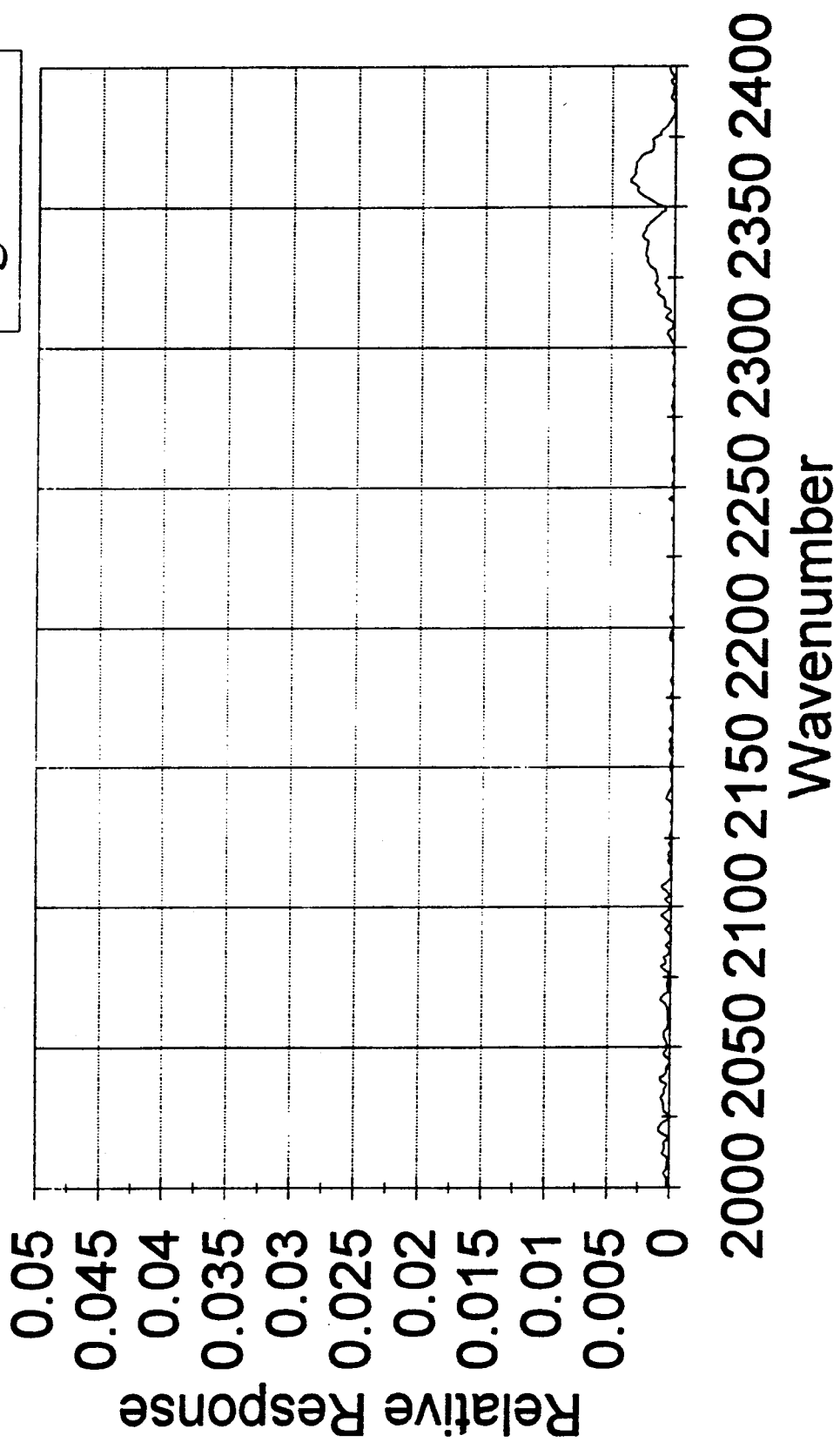
Figure 3D .5% Glucose in Water

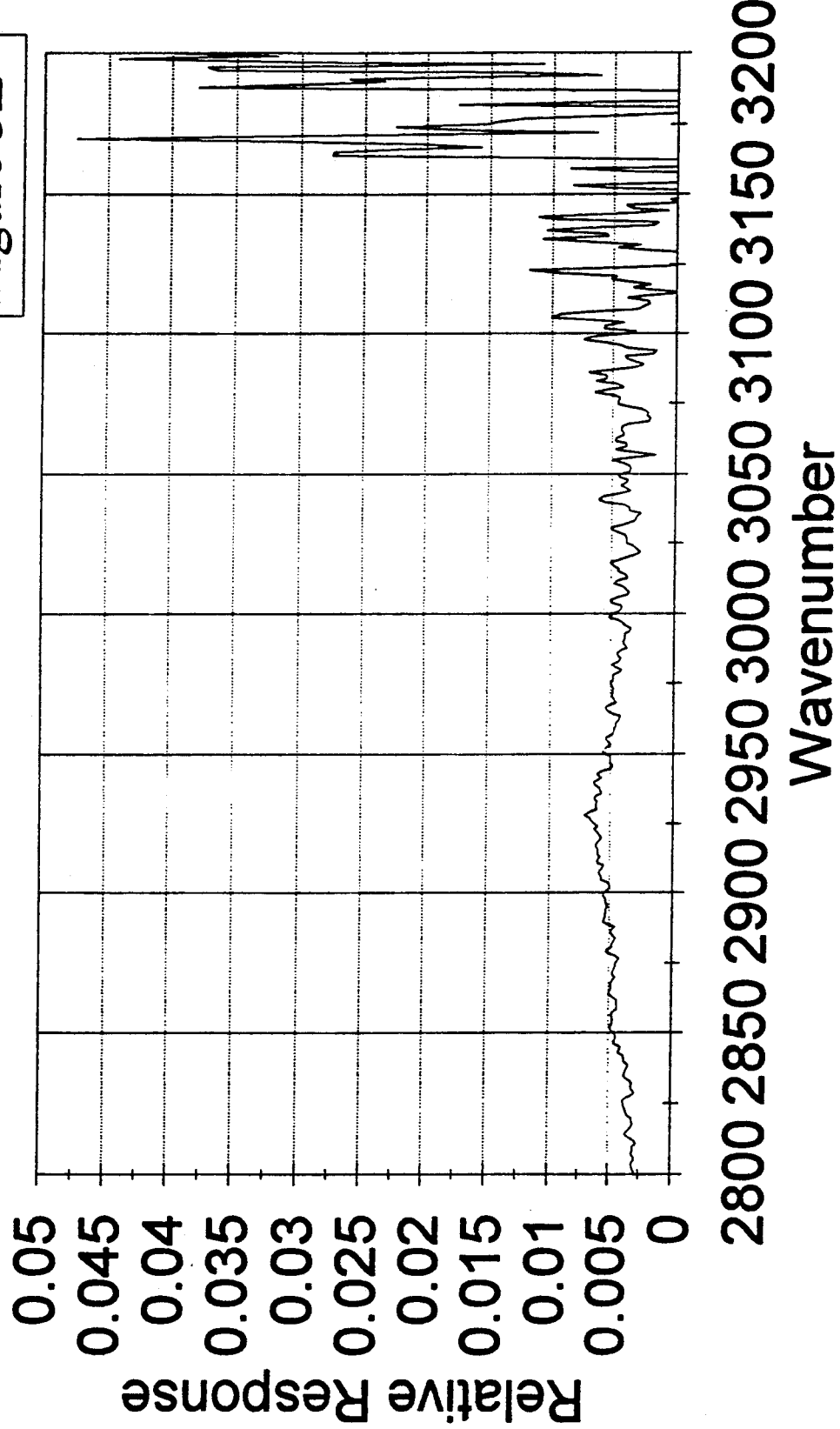
Figure 3E .5% Glucose in Water

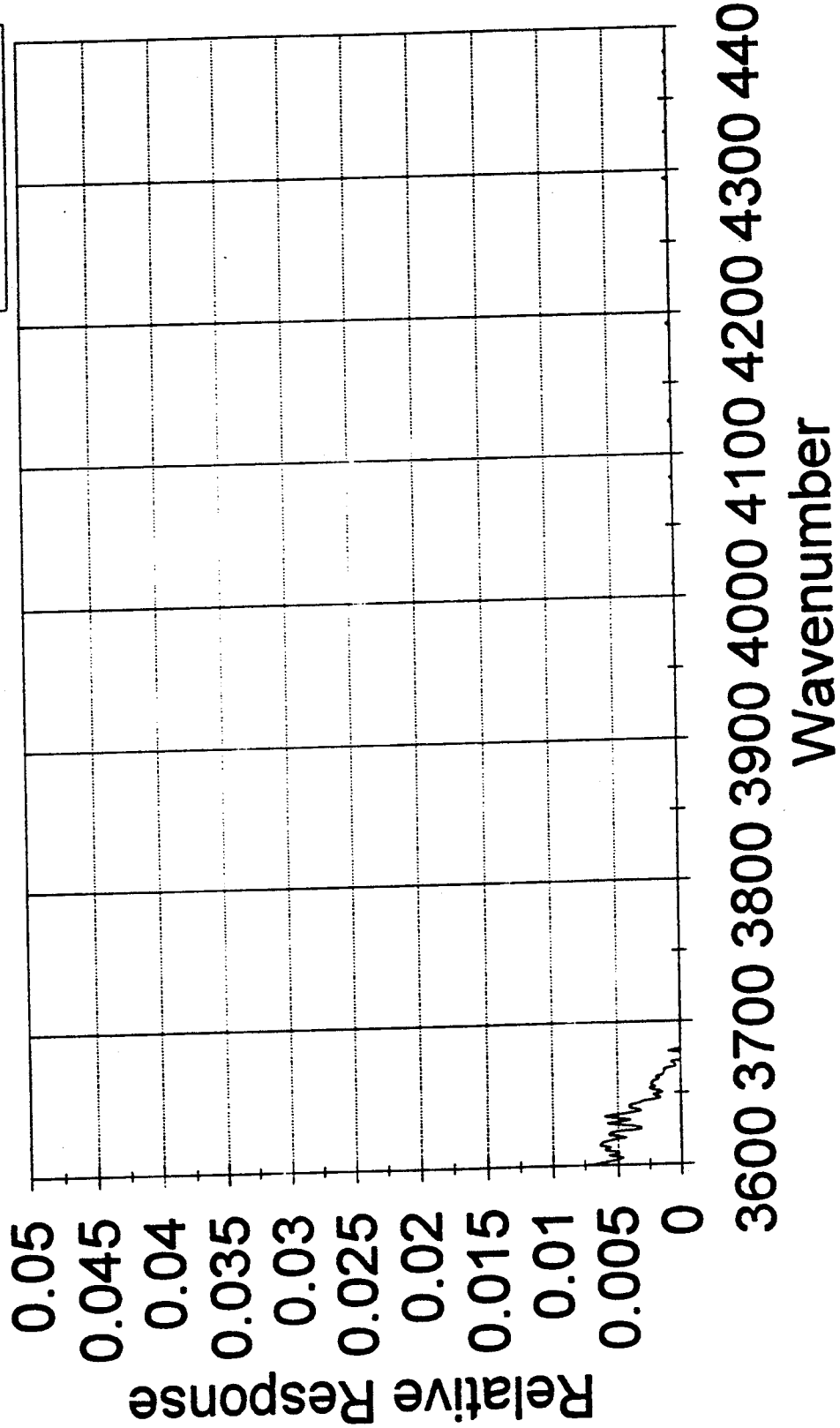

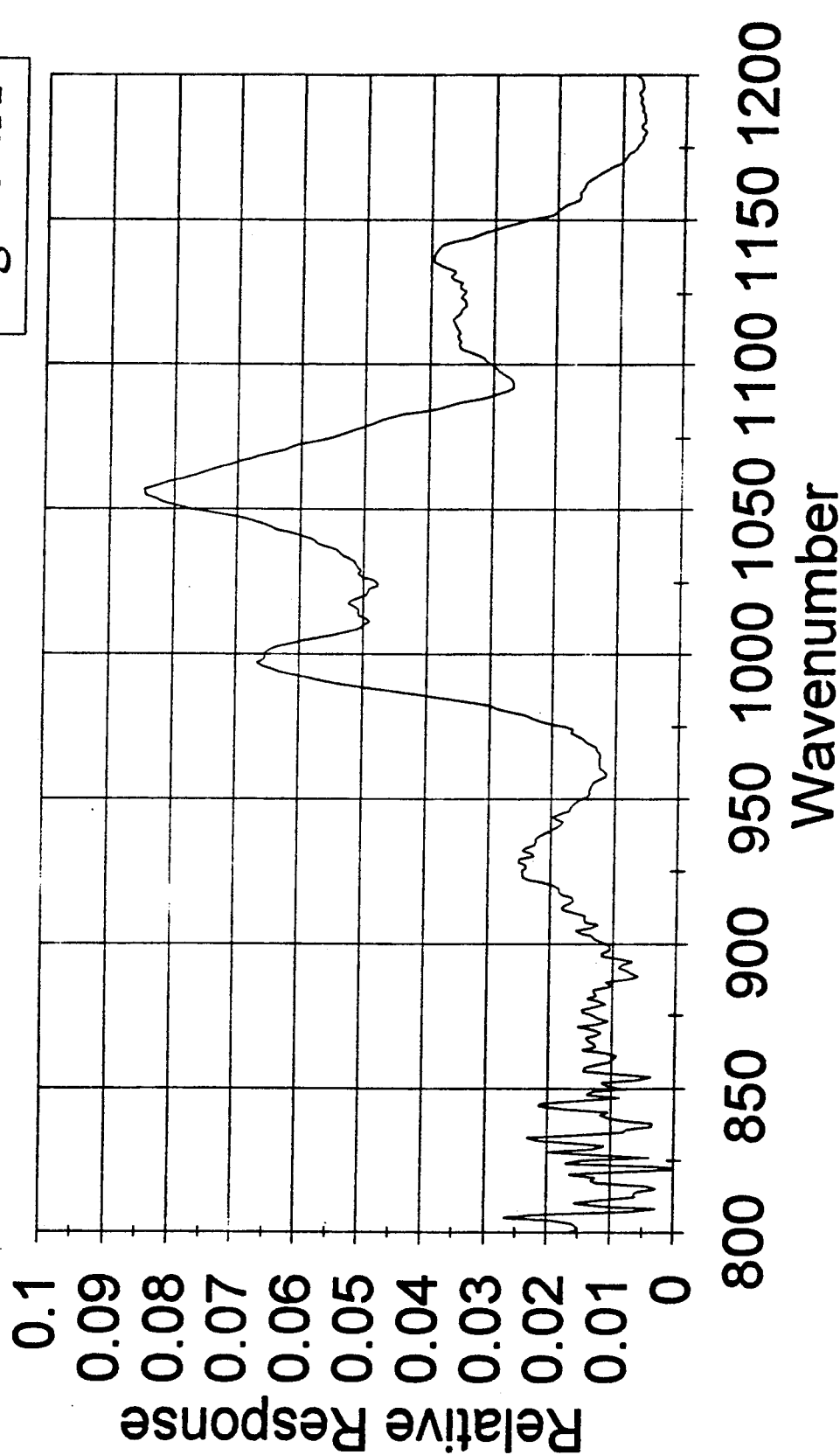

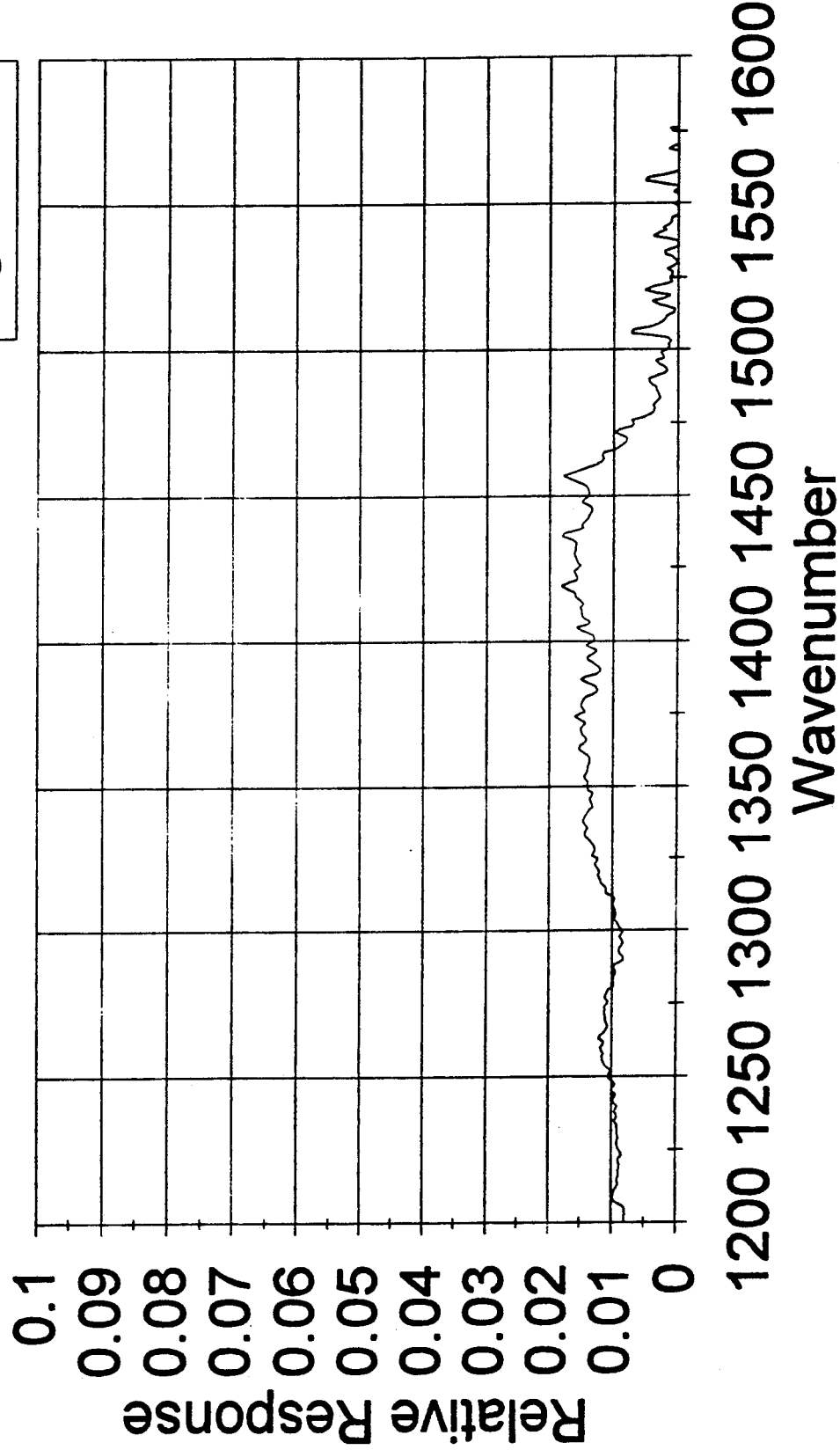

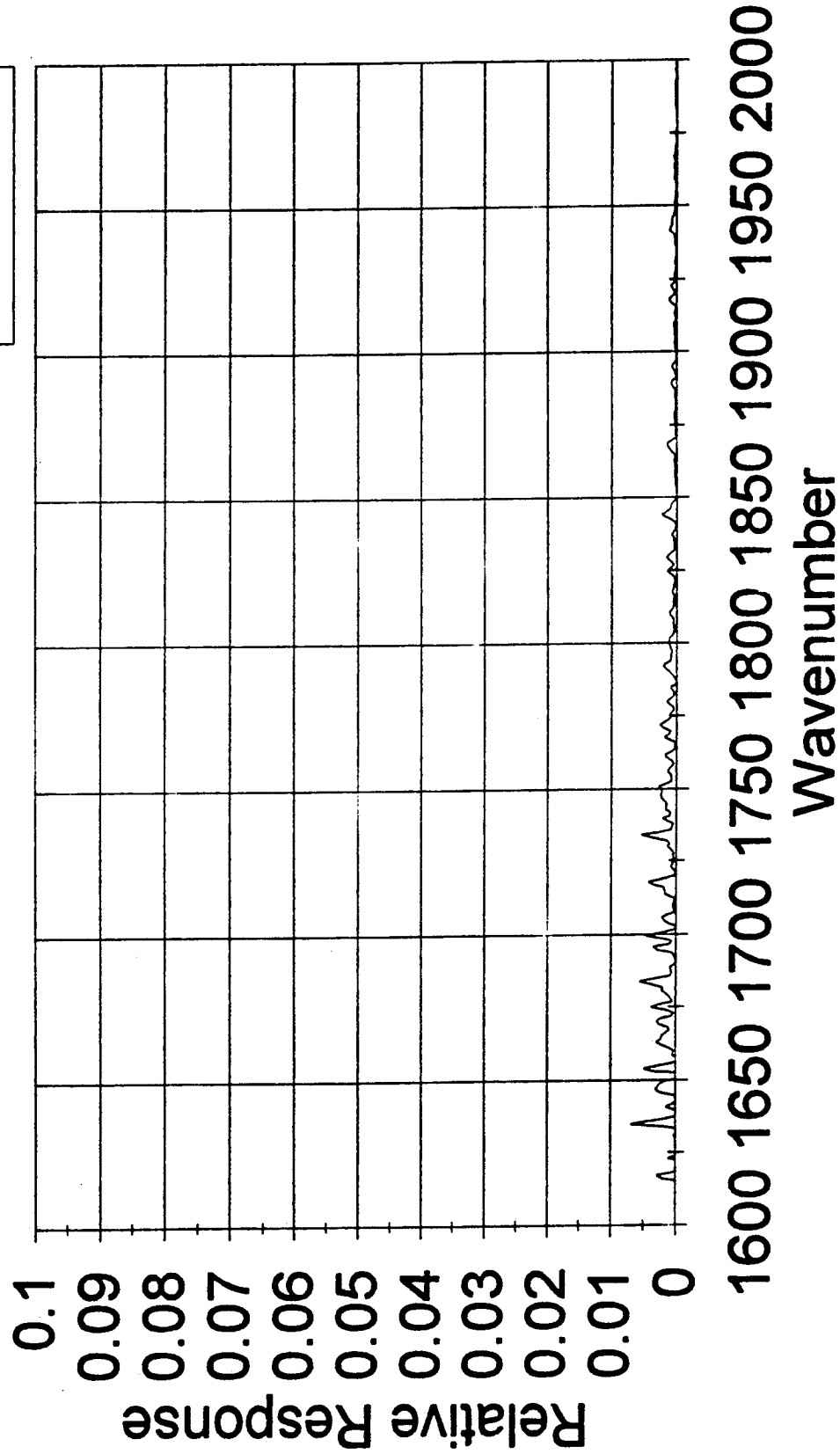

3% Sucrose in Water

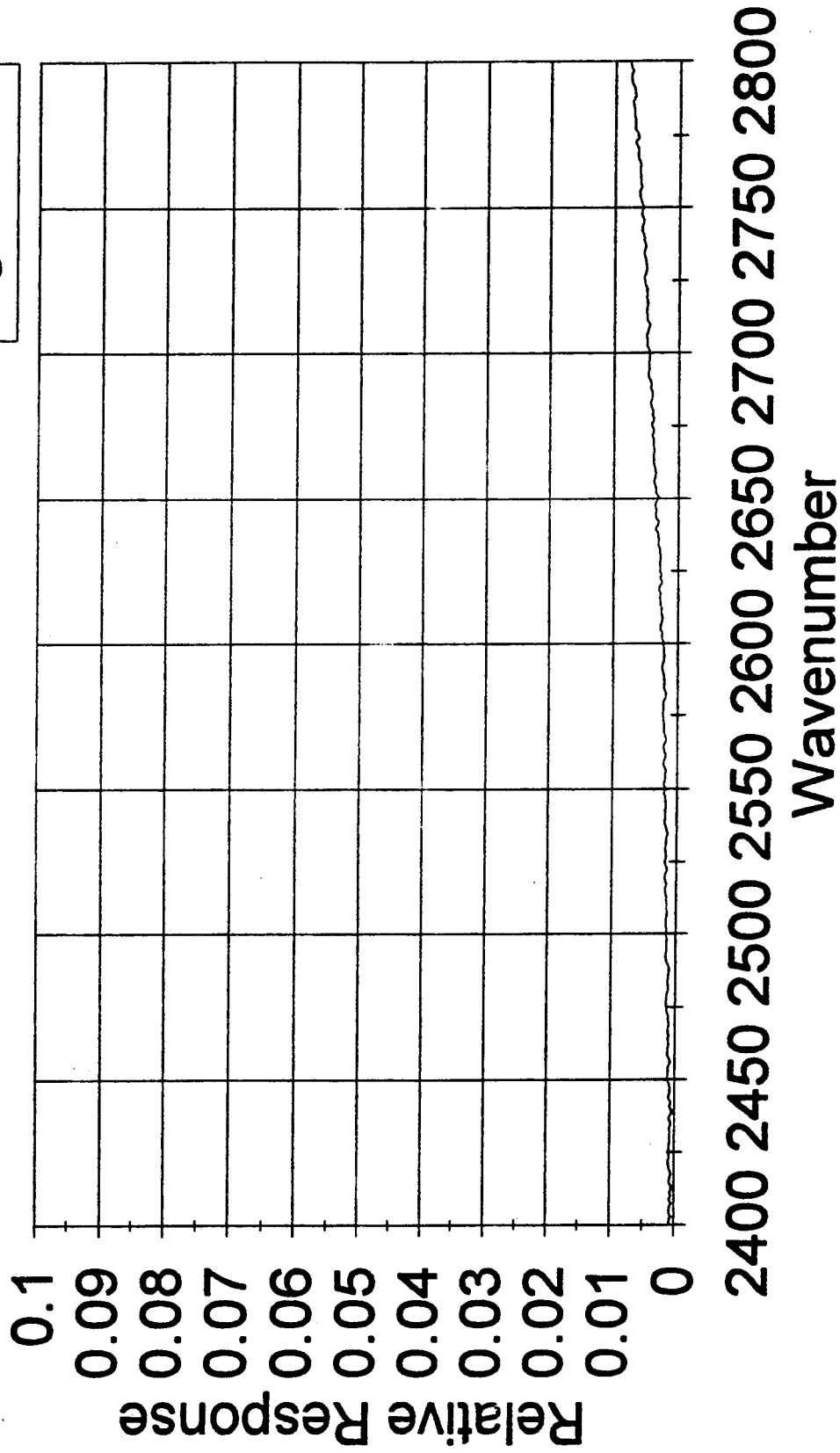

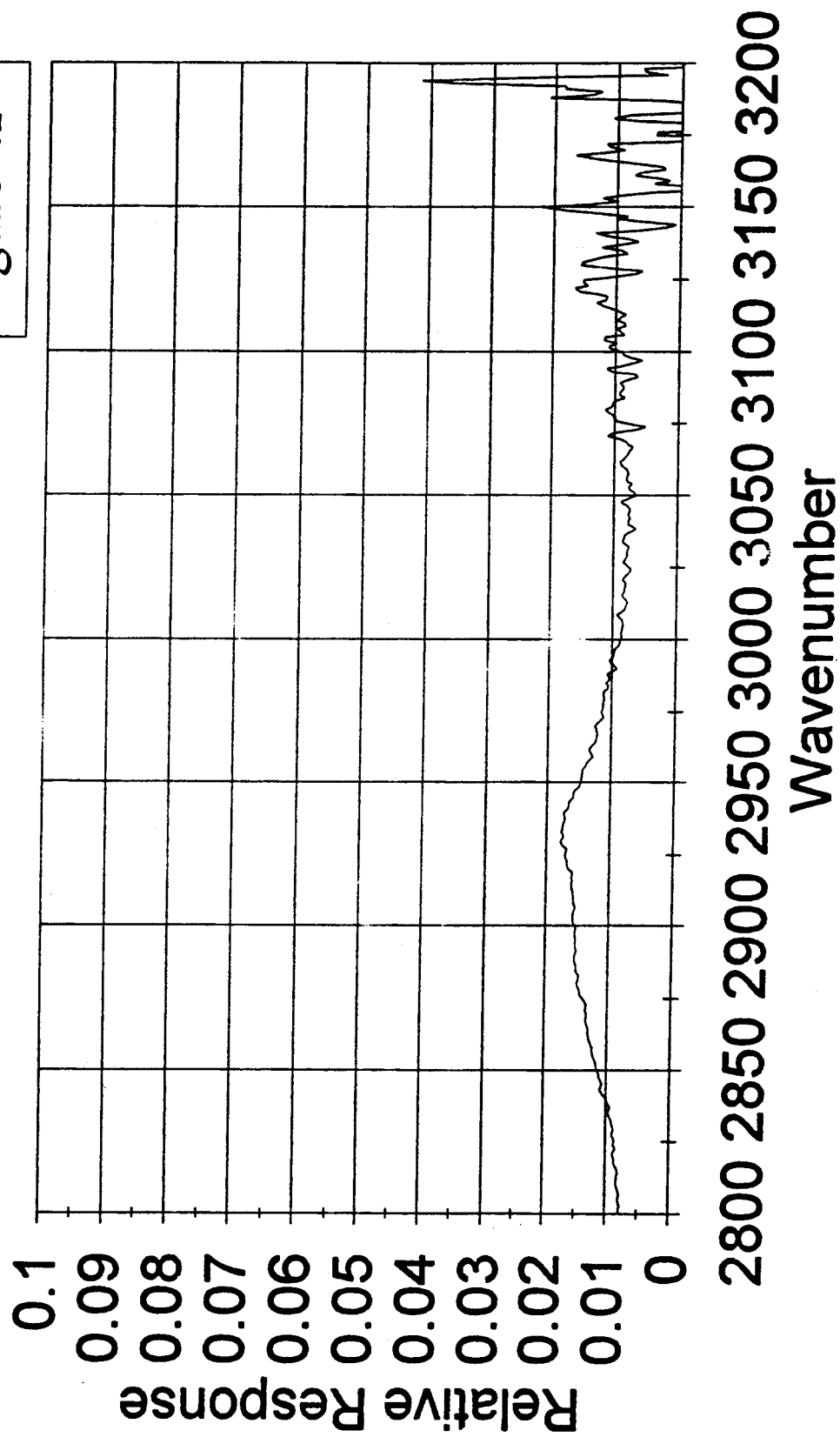

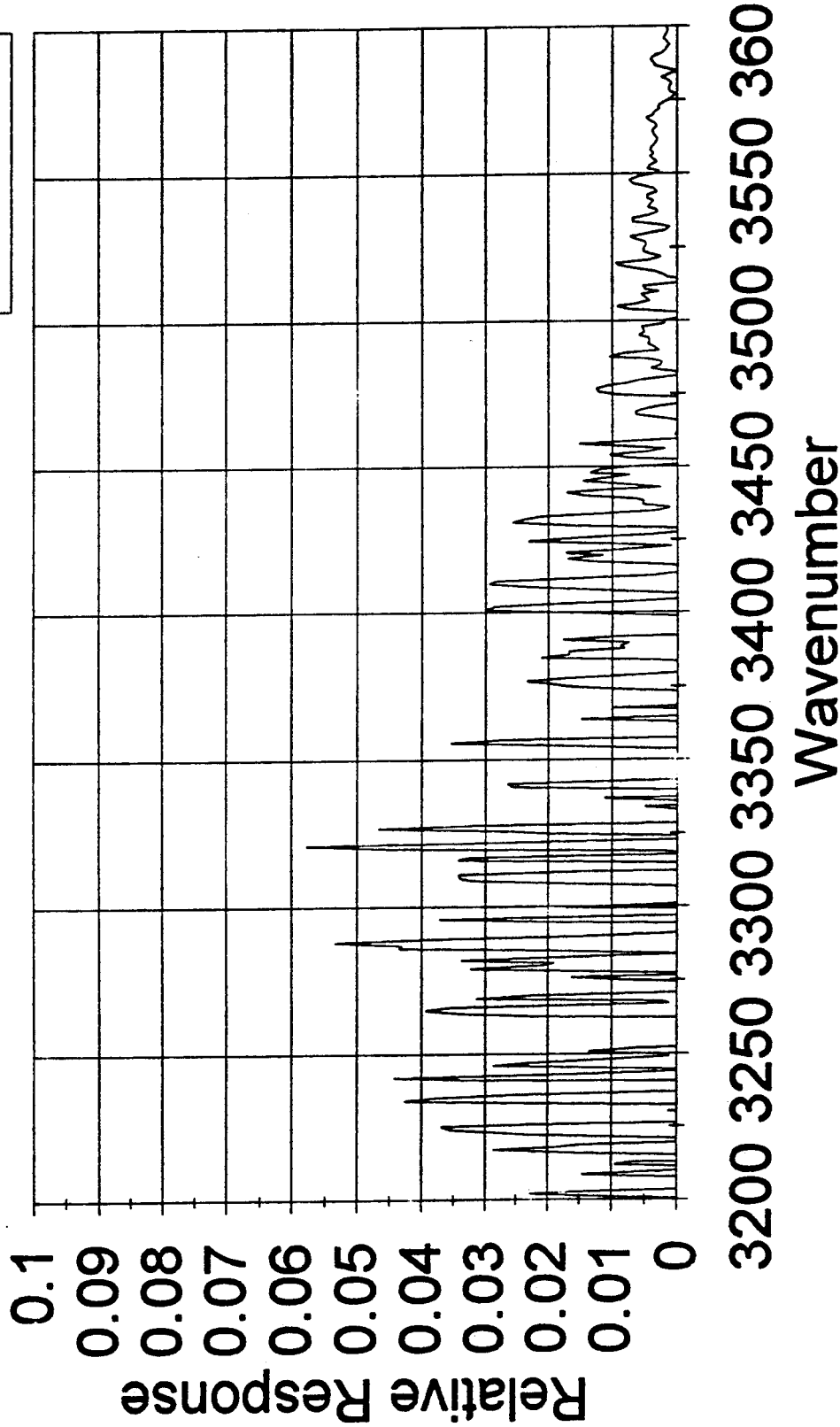

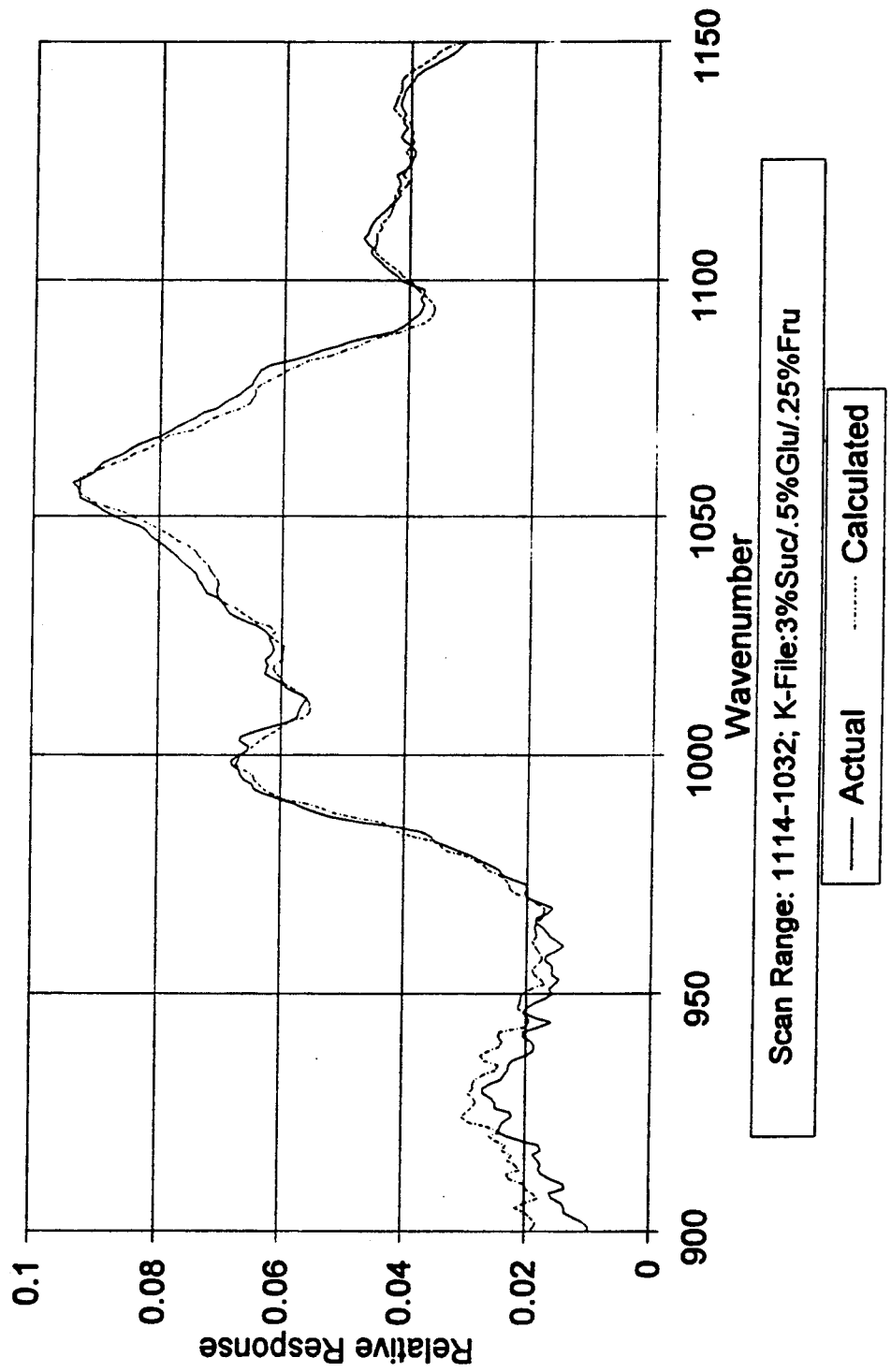

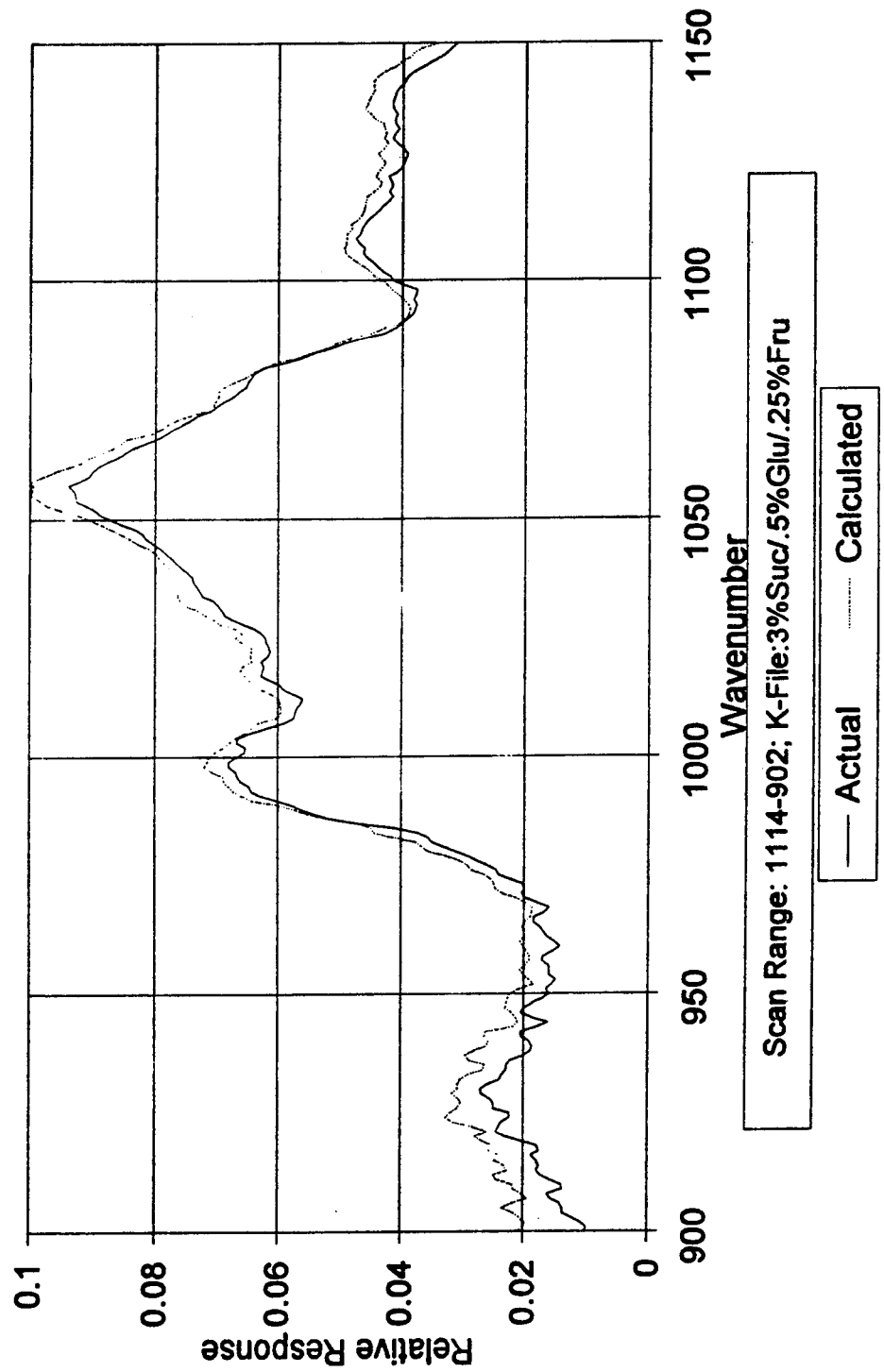

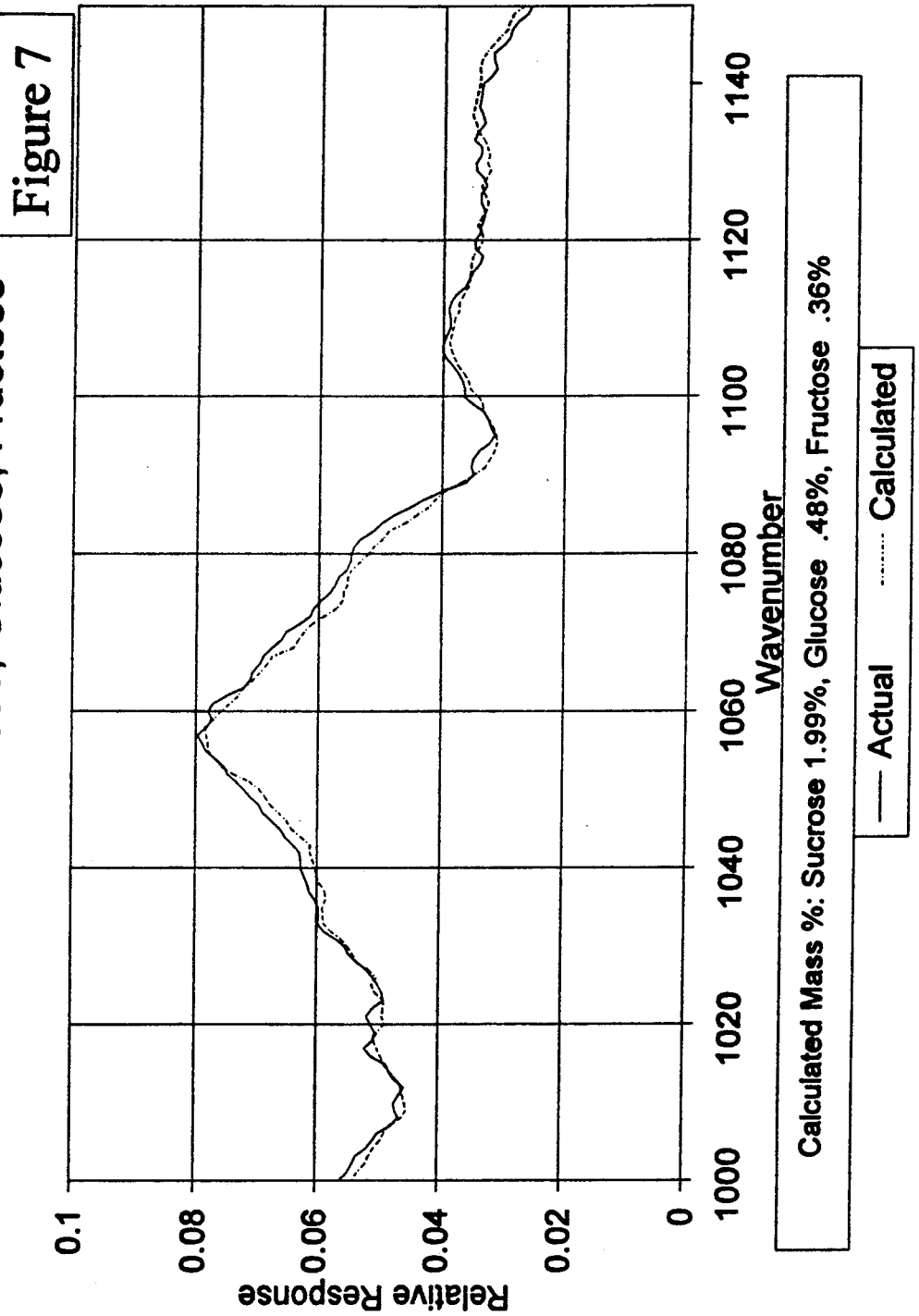

METHOD FOR MONITORING AND CONTROLLING A CHEMICAL PROCESS

BACKGROUND OF THE INVENTION

1. Field of the Invention

This invention relates to a method for monitoring and controlling a chemical process essentially instantaneously based on real time measurements of the concentration of reactants or products produced by the process, or both.

2. Background Discussion

There are many chemical processes which require physical parameters to be altered based on the concentration of reactants in the process or products produced by the process. Frequently, temperatures, pressures, flow rates, pH and other physical parameters of the process must be changed to optimize the operation of the process. (As used herein chemical process(es) shall mean any process wherein the concentration of reactants or products produced by the processes changes. It includes in vitro and in vivo biochemical, nuclear, metallurgical, petrochemical, etc, processes.)

Conventional monitoring and control techniques are unable to measure the concentration of reactants, the products produced by the process, or both, with sufficient speed to then regulate process parameters based on the measured concentrations. One technique used to measure the concentration of reactants is electromagnetic radiation absorption technology. Over the range of the electromagnetic spectrum, all chemicals absorb or reflect "light" in a unique way that is characteristic of the structure of chemical being examined and its concentration in a mixture of different chemicals. For our purposes, light includes all regions of the electromagnetic spectrum from x-rays, UV, visible, infrared to microwaves. For example, one may determine the concentration of sucrose in water by spectroscopy, a technology wherein, for example, an aqueous sucrose solution is exposed to infrared light (IR) at different, discrete wavelengths.

The absorption spectra (the level of light absorption over a range of different, discrete wavelengths of light) is characteristic of the aqueous sucrose solution. The spectra is usually described in terms of the wavelength of electromagnetic radiation, for example, from 1 to 100 micrometers ($\mu$m). In spectroscopy, one frequently finds it useful to use a slightly different measure for the spectral position known as the wavenumber. The wavenumber, in $cm^{-1}$, is related to the wavelength in $\mu$m by 1/10,000, that is 1 $\mu$m is 10,000 $cm^{-1}$ and 10 $\mu$m is 1,000 $cm^{-1}$. Conventional Fourier Transform-IR technology is routinely capable of scanning from 1.2 $\mu$m to 100 $\mu$m in as little as ⅛ second with a resolution of $2.5 \times 10^{-5} \mu$m (0.25 $cm^{-1}$). For most purposes, including the purposes of the present invention (on-line chemical control and monitoring), a resolution of 2.0-4.0 cm and scan speed of 1-10 seconds is sufficient. This allows use of less expensive equipment since one pays a premium for speed and resolution.

The governing principle behind current quantitative analytical methods of transmission or absorption measurement instruments, in which realm IR analysis falls, relies on a relationship known as the Bouguer-Beer-Lambert Law. Many sources simply call this Beer's Law. In the simplest form it is written:

$$A = abc \quad [1]$$

where A is the absorbance, a is the molar absorptivity, b is the pathlength, and c is the concentration. Since the amount of energy absorbed is related to the number of molecules, the concentrations involved are molar quantities such as moles per liter or mole fraction. A mole of a material is a fixed number of molecules, e.g., $6.023 \times 10^{23}$ if the weight (called the molecular weight in this case) is given in grams. The molar absorptivity is the absorbance expected when 1 mole of a particular compound is present at the particular wavelength that the measurement is made.

Equation [1] is normally assumed to hold for every discrete wavelength for which the instrument can distinguish adjacent wavelength intervals. For example, with a 2.0 $cm^{-1}$ resolution, it is possible to distinguish reproducible differences as close as 1.0 $cm^{-1}$. Thus, a spectra from 450 $cm^{-1}$ to 4400 $cm^{-1}$ would have 3,951 points and equation [1] would be assumed to apply to each of these points.

It is frequently useful to combine terms in equation [1] into the form:

$$A = kc \quad [2]$$

where k now represents a "constant" which combines the molar absorptivity and the pathlength. By measuring the absorbance, A, of samples with differing amounts of material at various concentrations, c, one can calculate k. When k does not vary over a range of concentrations, the samples and the material being measured are said to obey Beer's Law.

Once k is known, unknown samples of the material are determined simply by measuring the Absorbance, A, and dividing by k for each discrete wavelength for which the measurements are made and for which Beer's Law has been shown to apply.

One can measure transmission as well as absorbance. The two quantities are related by the expression:

$$A = ln(1/T) \quad [2]$$

where T is transmission. The transmission is defined as the fractional reduction in intensity of a beam of electromagnetic radiation passing through the medium containing the absorbing material. Formally, it is:

$$T = I/I_0 \quad [4]$$

where I is the measured intensity with the absorbing material in the beam and $I_0$ is the measured intensity without the absorbing material. Sometimes Beer's Law is written:

$$I = I_0 e^{-abc} \quad [5]$$

which is the algebraic combination of equations [1], 3] and [4]. It is much more convenient to analyze results using equations [1] avoiding the use of exponentials.

When one has a mixture of materials, equations [1] or [2] is usually held to be applicable to each of the materials separately. That is, for a mixture of 3 materials at each wavelength or wavenumber:

$$A = k_1 c_1 + k_2 c_2 + k_3 c_3 \quad [6]$$

where the subscripts refer to the three components. Since equation [6] holds at each wavelength (or wavenumber), there are as many equations as wavelengths so the values at the selected wavelength (m) can be written as $A_m = k_{m1}c_1 + k_{m2}c_2 + k_{m3}c_3$. This could be, for example, a mixture of three gases moving through a gas cell attached to an FT-IR instrument or two solutes (such as sucrose and ethanol) dissolved in a solvent (such as water). In current practice, again assuming that Beer'-Law is valid, the $k_i$ would have been determined from previous experiments and thus the $c_i$ can be calculated if three sets of measurements are taken at three or more wavelengths. In current practice, the measurements over many wavelengths are used to find the "best fit" for $c_i$ using least squares or partial least squares regression analysis. There is no way of determining which series or ranges of wavenumbers is the best to use. This is done exclusively by trial and error based on the analyst's experience.

For a discussion of the state-of-the-art, the book "Fourier Transform Infrared Spectrometry" by Peter R. Griffiths and James A. de Haseth, John Wiley & Sons, 1986 is recommended. Chapter 10 in this book discusses quantitative analysis. Of particular importance is section IV on multicomponent analysis beginning on page 355. On page 356, the authors note that Beer's Law is a requirement for the analysis techniques they present.

There is also a four volume series edited by John R. Ferraro and Louis J. Basile. The series is entitled "Fourier Transform Infrared Spectroscopy" and is published by Academic Press, Inc. Volume 1 was published in 1978, Volume 2 in 1979, Volume 3 in 1982, and Volume 4 in 1985. The latest volume contains a contribution by P. C. Gillette, J. B. Lando and J. L. Koenig on "A Survey of Infrared Spectral Processing Techniques." They again state the requirements for Beer's Law as well as mention that least squares analysis is a preferred technique. Based on experimentation in connection with conducting chemical analysis which the present invention addresses successfully, the least squares and related techniques are highly overrated and are rarely the best techniques for looking at variable data or determining the "best fit" in analysis of spectral data. Further, Beer's Law rarely holds in practical systems, particularly in solvent systems or complex mixed gases or polymeric solids.

SUMMARY OF THE INVENTION

It is the objective of this invention to measure in real time the concentration of reactants and products produced by a chemical process and essentially instantaneously control the physical parameters of the process based on the concentration measurements to optimize the process. The term instantaneous can mean from a few seconds to a few minutes, depending on the speed required for the system under control. For a biochemical reaction, which takes days to complete, a few minutes is sufficiently instantaneous. For a rapid gas phase reaction, a few seconds would be needed.

The method of this invention has several features, no single one of which is solely responsible for its desirable attributes. Without limiting the scope of this invention as expressed by the claims which follow, its more prominent features will now be discussed briefly. After considering this discussion, and particularly after reading the section of this application entitled, "DETAILED DESCRIPTION OF THE PREFERRED EMBODIMENT," one will understand how the features of this invention provide its advantages, which include:

1. The mixture of chemicals being analyzed do not need to obey Beer's Law.
2. The "best" wavelength range for determining concentration is automatically located.
3. Answers are obtained based on statistical criteria, i.e., standard deviations and Chi-square.
4. The process is fast. Typically, it takes a few seconds on a 12 Mhz 80826 microcomputer with math coprocessor and hard disk to perform the final analysis. Each of the steps can also be automated and are also fast.
5. The method works for any spectrometer and with any combination of solvents and solutes to the precision set by the limits of the mathematical analysis employed. That is, if a statistically significant answer is possible for a particular combination of instrument, cell, and mixture of chemicals to a desired level of precision, the method of this invention has the best mathematical chance of finding useful ranges of the spectra and solutions to the analysis problem.

There are a number of different types of IR instruments available, including grating, prism, and Fourier transform (FT) instruments. Although grating or prism IR instruments may be used for the purposes of the present invention, the FT-IR instrument is preferred because it can scan a wide range of IR frequencies in a very short time. The methods to be described are also applicable to other portions of the electromagnetic spectrum besides IR, for example, UV, visible and microwaves.

STATISTICAL DECONVOLUTION

In accordance with this invention, a modified Chi-Square fitting mathematical technique is employed in analyzing spectral data. For purposes of this spectral analysis, points are better weighted by the inverse of the standard deviation at a particular wavelength rather then the minimum of the squares of the deviations as in the least squares analysis. The analytical technique used in this invention is related to the Chi-Square fitting mathematical technique and it provides a much more powerful method and is a major improvement in analysis of spectral data.

In the modified Chi-Square technique of this invention, obtaining the spectrum is repeated many times, for example, 32 or 64 replicates. The average and standard deviation are then calculated at each wavenumber (or wavelength). The calculation to find the best values of the concentrations from an equation like equation [6] are fit by weighting the points in the spectrum with the lowest standard deviation more than points with the higher deviations. This results in improved accuracy and precision.

The modified Chi-Square technique employed in the present invention is new in the context of spectroscopy. The known Chi-Square technique has been particularly modified to fit into the method of this invention for analyzing spectral data using a conventional general purpose computer and FT-IR instrument. An excellent discussion of the Chi-Square technique, in general terms, appears in "Numerical Recipes, The Art of Scientific Computing," by William H. Press, Brian P. Flannery, Saul A. Teukosky, and William, T. Vetterling, Cambridge University Press, 1986. Chapter 14 in the book does a good job of explaining the short falls of the overused least squares techniques and provides a particularly robust (in the mathematical sense) technique for carrying out a Chi-Square fit known as Singular Value Decomposition (SVD). This technique assures meaningful answers even when the equations being solved are unstable.

One disadvantage of the Chi-Square technique is that the standard deviations of the measured solution are needed at each wavenumber. This would normally mean taking many spectra of the same sample. Since one purpose of our process is for continuous and rapid monitoring, a means was developed to avoid making multiple determinations.

It was found that the errors in the spectra are mostly a function of the instrument, the cell in which the sample resides, and the particular nature of the chemical solution being analyzed. That is, a sample of water, sucrose, ethanol, and glucose in a particular cell in a particular instrument will have similar errors over a wide range of concentrations. Thus, in determining unknown samples of sucrose, glucose, ethanol in water, one can use the standard deviations from previous measurements on known solutions made while calibrating the instrument to determine the k's of equation [6].

One can always improve on the algorithm, either the Chi-Square or the least squares, by selecting specific wavelengths at which the calculations are done. That is, by looking at the separate spectra of the materials to be determined in combination, one can find regions of the spectrum where there is just the right amount of overlap or interference to make the final absorbance be a "comfortable" sum of all the materials. To better understand this, consider a gas phase spectrum comprising a mixture of nitric oxide, carbon monoxide, and carbon dioxide. In the gas phase, it is possible to find regions of the spectrum where characteristic absorbance lines of only one of these items shows up. Since only one item shows up, one can use equation [1] separately for each component by only analyzing for that gas over that restricted wavelength region. It is this technique that made gas phase work easier and this logic that made artisans in this field seek simpler analytical methods for liquid or solid phase problems. The present invention provides such a simpler method using regions of the spectrum where the absorbance due to a complicated mixture is strongly influenced (overlapped) by many of all of the components of the mixture.

Surprisingly, in the case of accurate and precise multicomponent analysis using equation [6], or a similar equation for however many components one wishes, the best results appear in wavelength regions where the terms $k_1$ and $c_1$ have approximately equal values in the expression $(k_1 c_1)$. One can determine the $k_1$ separately for each component beforehand. The region of the spectra that has k values for each component multiplied by the expected concentration, approximately equal to each other, will be the best range in which to work. For example, in a mixture of sucrose, glucose, and fructose in water, this region is 920 to 1250 cm$^{-1}$. This type of conclusion, for each set of materials studied, is reached naturally by use of the methods of this invention, but cannot be predicted.

Even more surprising was the discovery that once one became used to exploring the values of k versus wavenumber (or wavelength) the files of k's could be kept as a function of concentration and the best k for the values nearest the concentration range being sought could be automatically used with a very simple computer algorithm. This means that adherence to Beer's Law is no longer a requirement for the analysis. One simply must know the value of the k's as a function of concentration for each material separately or as modified by interactions with each other as shall be explained below. These k values are stored in data files in the memory of the computer as ranges of interest and then equation [6] is solved using the k values that best meet the concentration range of the mixture. After one calculation, when concentrations have been found, the k values closest to that concentration, or new k values found by non-linear cubic spline interpolation between k values above and below, are used to recalculate the concentrations. This procedure is repeated until the method converges to the desired degree of precision.

EXAMPLE

The modified Chi-Square technique of this invention is best explained with reference to a concrete example such as analysis of a mixture of sucrose, glucose, and ethanol in water. The method steps are:

1. Make up a series (5) of individual calibration solutions or samples of each of the components at a known concentration in water, spanning the concentration range of interest, for example, 1-10 weight percent. Take the spectra of these calibration samples over a selected range of interest, for example 600 cm$^{-1}$ to 4400 cm$^1$, and determine k's for each sample at each concentration and at each wavenumber from:

$$A = k_{water} c_{water} + k_{sample} c \qquad [7]$$

and $$c_{water} + c = 1.0 \qquad [8]$$

Equation [8] is true because the concentrations are in mole fractions which must add up to 1.0. The $k_{water}$ is simply the absorbance of the background water. This is obtained by taking a spectra of pure water alone in the same cell. The range for the spectra can be in any portion of the spectra in which one expects to find significant information. In this case, based on general knowledge of the spectra of the components, the range of 600 cm$^{-1}$ to 4400 cm$^{-1}$ was chosen. This means that one has a file of k's for each of the compounds, sucrose, glucose, and ethanol for each wavenumber. This process repeated 5-20 times, optimally 10, such that one can obtain statistically significant values of the k's at each concentration.

2. Use the same spectra from 1 to obtain a standard deviation file. For example, the 10 spectra of sucrose (without modification) are averaged and the standard deviation is obtained at each wavenumber. The standard deviation of the set of three (glucose, sucrose, ethanol) are then averaged (or summed) to obtain the standard deviation file to be used for the Singular Value Decomposition (SVD) fit of the data in step 3 below. Generally the average is preferred. However, the sum would give the most conservative estimate of the goodness of fit, which is also available from the covariance matrix in the SVD technique.

3. Make up one mixture of known composition and use this as a "mock unknown" or calibration sample mixture. Measure its spectrum and then analyze it according to [6] and the SVD technique over a range of wavenumbers covering all significant features of the absorbance spectra of the previous separate knowns used in 1 and 2. For example, the range 800 cm$^{-1}$ to 1500 cm$^{-1}$ could be a good wide starting choice. The SVD technique provides a statistical measure of the goodness of fit in two ways. First, it provides the Chi-Square statistic and second, it provides a standard deviation for each determined quantity. In this case, we are determining the mole fractions of water, sucrose, glucose, and ethanol, so each of these would have a standard deviation associated with it which are compared to the actual values. The range of wavenumbers used is reduced and/or moved in the spectrum to find the range of wavenumbers that provide the lowest Chi-Square statistic and lowest standard deviations. In the example, this could be the range 994 $cm^{-1}$ to 1100 $cm^{-1}$. The exact range will differ from instrument to instrument and cell to cell, but the technique will find the best range for the particular combination one has available. The computer can be programmed to move the range randomly or systematically. The method will always find the best range of those examined based on the Chi-square value and standard deviations. The range can be varied until a desired degree of precision is achieved.

4. One can now measure true unknowns. The measurement is made normally and the first analysis is made using the k s determined form knowns from step 1 that are close to the anticipated concentrations. The standard deviations are also used from the same files that provide the k's. When the answers are obtained from the SVD technique, they are examined to see if there is a set of k's determined from any of the non-solvent unknowns (sucrose, glucose, ethanol) at a concentration closer to the answer just found than were those used in determining the answer. If a set of k's from a closer concentration is available, it is used and the concentrations recalculated. This procedure is repeated until the closest k's are used. It is preferred to refine this procedure by interpolating between k's such that the final answer is as close to the concentration corresponding to the k's as one would like it to be, e.g., within 1% or so. For mixtures of gases, equations [7] and [8] are replaced by the simpler expression of equation [2].

Use of the Modified Chi-Square Technique

The modified Chi-Square technique of this invention is ideal for on-line monitoring and control of a chemical process. Any suitable computer using, for example, an 80826 microprocessor and equipped with analog to digital (A/D) and digital to analog (D/A) interfaces, may be use to implement this modified Chi-Square technique. The computer is attached to both the D/A and A/D boards via a parallel port (D/A) and a serial port (A/D). A second serial port is attached to the FT-IR instrument.

A chemical stream from the process of interest is constantly flowed through the cell in the FT-IR instrument. For example, this could be the exhaust of a combustion device, the broth in a fermenter, water being discharged from a factory, a chemical process, etc. The same process is also monitored with various probes to measure temperature, pressure, flow, pH, dissolved oxygen, humidity, density, weight, etc.

The probes monitoring the physical parameters of the process are connected to the A/D board, which has an on board microprocessor to act as storage and shipping center of the information to the host 80826 microprocessor. The host computer need not use an 80826 microprocessor and, in fact, all of the hardware and software is designed to be portable to any computer environment. The A/D board collects the probe information until it is polled by the host computer. The FT IR instrument is also commanded by the host computer. In this manner, the host computer can regulate the flow of both chemical and physical input information and create files and displays of all of these parameters as a function of time.

The host computer also contains outputs through the D/A board connected to the parallel port that allows the chemical and physical information to be used to control switches and valves of the control instrumentation for the process. The process of this invention performs the integrated tasks of monitoring and control based on measurements of chemical concentrations as well as physical criteria. Until now, processes that use chemical composition criteria have been limited to those which use electrodes (which are relatively inaccurate and require frequent replacement) or to those which use mass spectrometry or combination gas chromatography and mass spectrometry. These later cases are slower in response and more costly and frequently require either removal or pretreatment of the sample. Using FT-IR instruments, the sample essentially never leaves the system being monitored, the sample requires no pretreatment, and the answers are as rapid as the scans. Including analysis processing, the answer is available in seconds compared to minutes or hours for the other instrument techniques and much more accurately and for a much wider range of chemicals when compared to the very limited electrode technique.

DESCRIPTION OF THE DRAWING

The preferred embodiment of this invention, illustrating all its features, will now be discussed in detail. This embodiment depicts the novel and non-obvious method of this invention depicted in the accompanying drawing, which is for illustrative purposes only. This drawing includes the following figures (Fig.), with like numerals indicating like parts:

FIGS. 2A through 2E is the absorption spectra for a 0.25 weight percent aqueous fructose solution taken over a range of wavenumbers between 800 and 2800.

FIGS. 3A through 3G is the absorption spectra for a 0.50 weight percent aqueous glucose solution taken over a range of wavenumbers between 800 and 4400.

FIGS. 4A through 4H the absorption spectra for a 3.0 weight percent aqueous sucrose solution taken over a range of wavenumbers between 800 and 4400.

FIG. 5 is the absorption spectra of an aqueous solution containing known concentrations of sucrose (2.5%), glucose (0.59%), and fructose (0.30%), a calibration mixture sample, taken over a range of wavenumbers between 900 and 1150 using k values from data files 3% sucrose/0.5% glucose/0.25% fructose over the scan range 1114–1032. The solid line shows actual data points, the dotted line shows calculated data points.

FIG. 6 is the absorption spectra of an aqueous solution containing known concentrations of sucrose (2.5%), glucose (0.59%), and fructose (0.30%), a calibration mixture sample, taken over a range of wavenumbers between 900 and 1150 using k values from data files 3% sucrose/0.5% glucose/0.25% fructose over the scan range 1114–902. The solid line shows actual absorbances points, the dotted line shows calculated absorbance points.

FIG. 7 is the absorption spectra of an aqueous solution containing unknown concentrations of sucrose, glucose, and fructose taken over a range of wavenumbers between 1000 and 1160. According to the method of this invention, the concentrations were determined to be sucrose 1.99%, glucose 0.48%, and fructose 0.36%. The solid line shows actual absorbance points from the unknown measured spectrum, the dotted line shows calculated absorbance points using the values of concentration determined by the method of the invention.

DESCRIPTION OF THE PREFERRED EMBODIMENT

Figure 1:
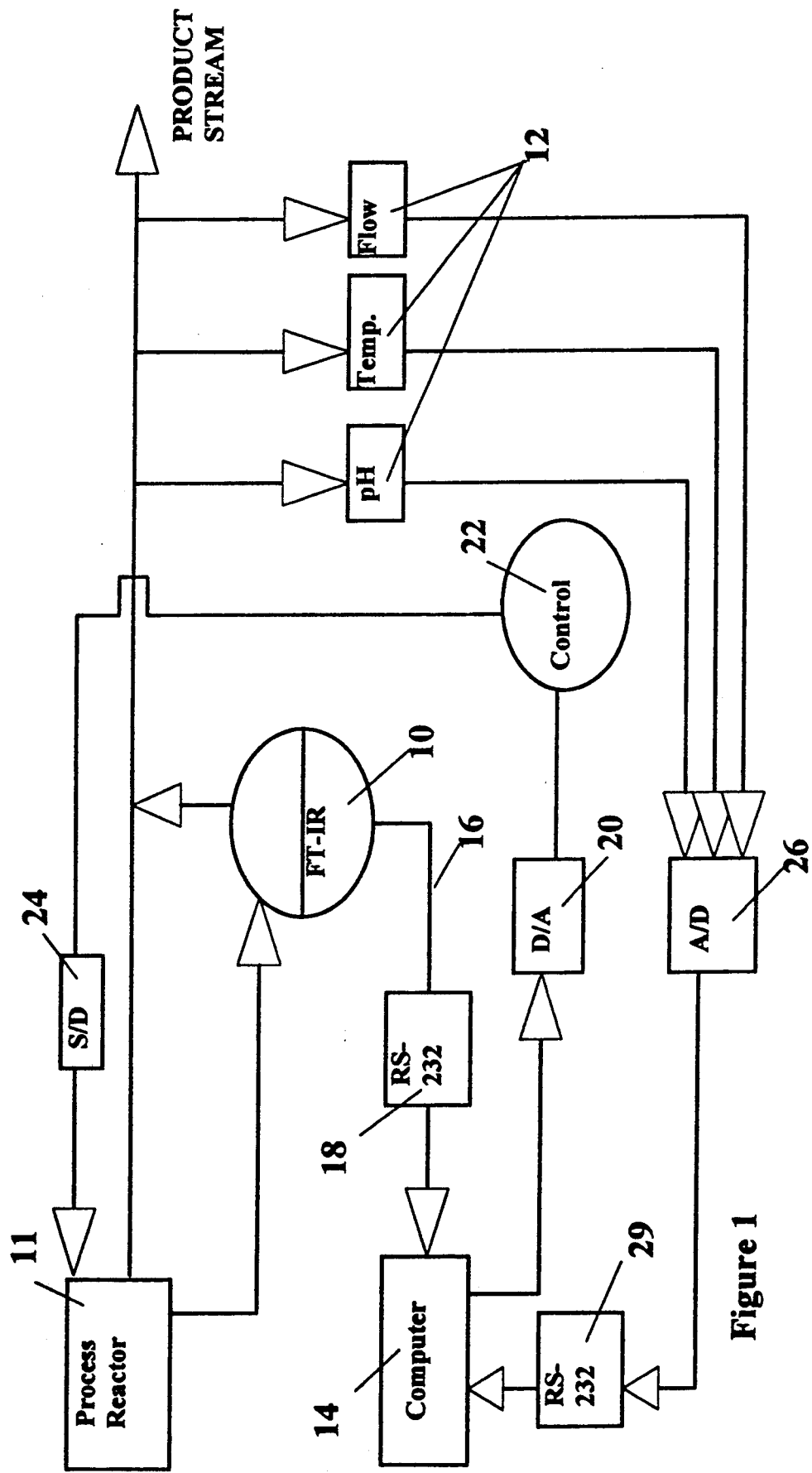
FIG. 1 is a schematic diagram of a chemical process employing the monitoring and control method of this invention.
Figure 2A:
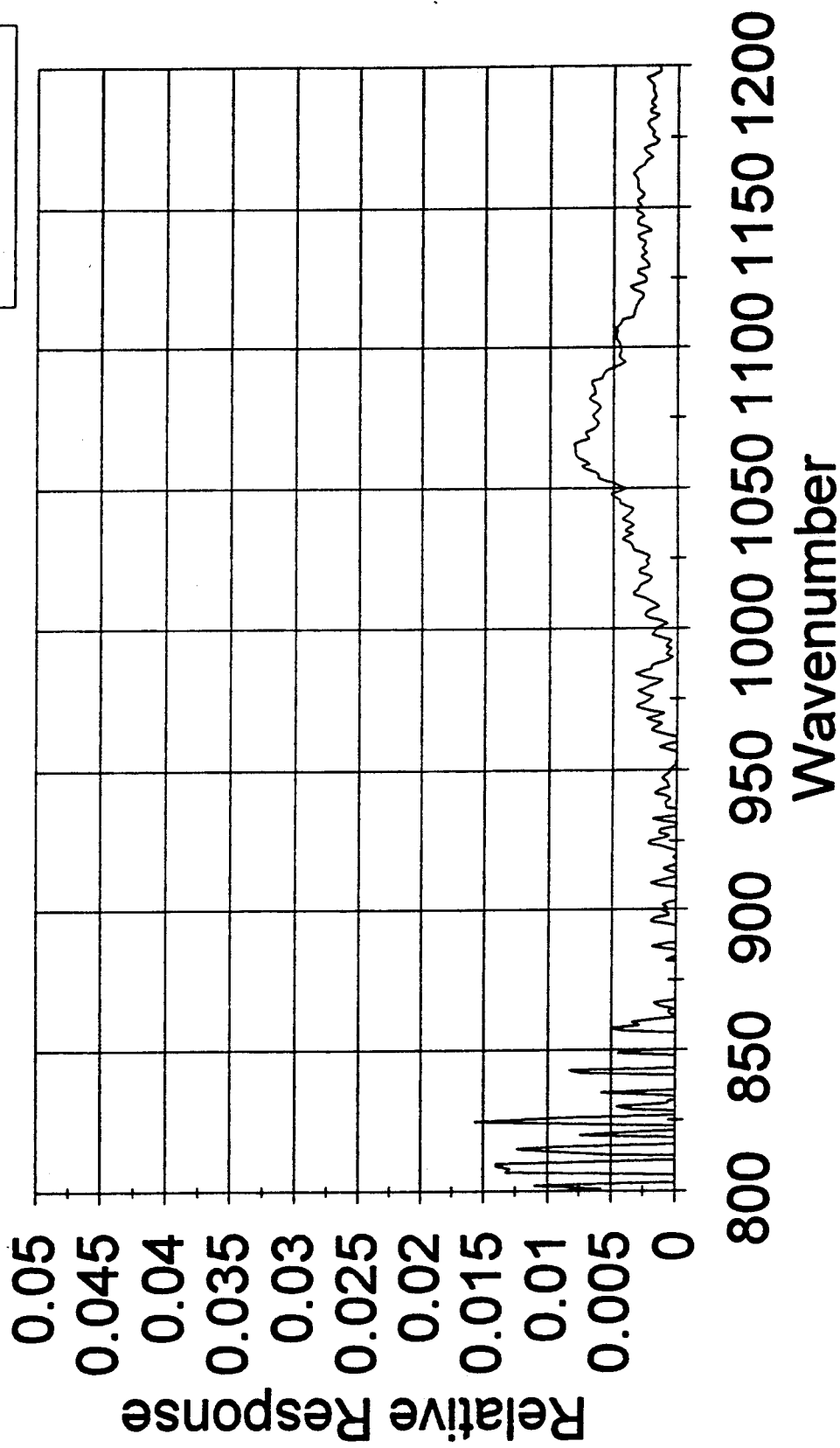
Figure 2C:
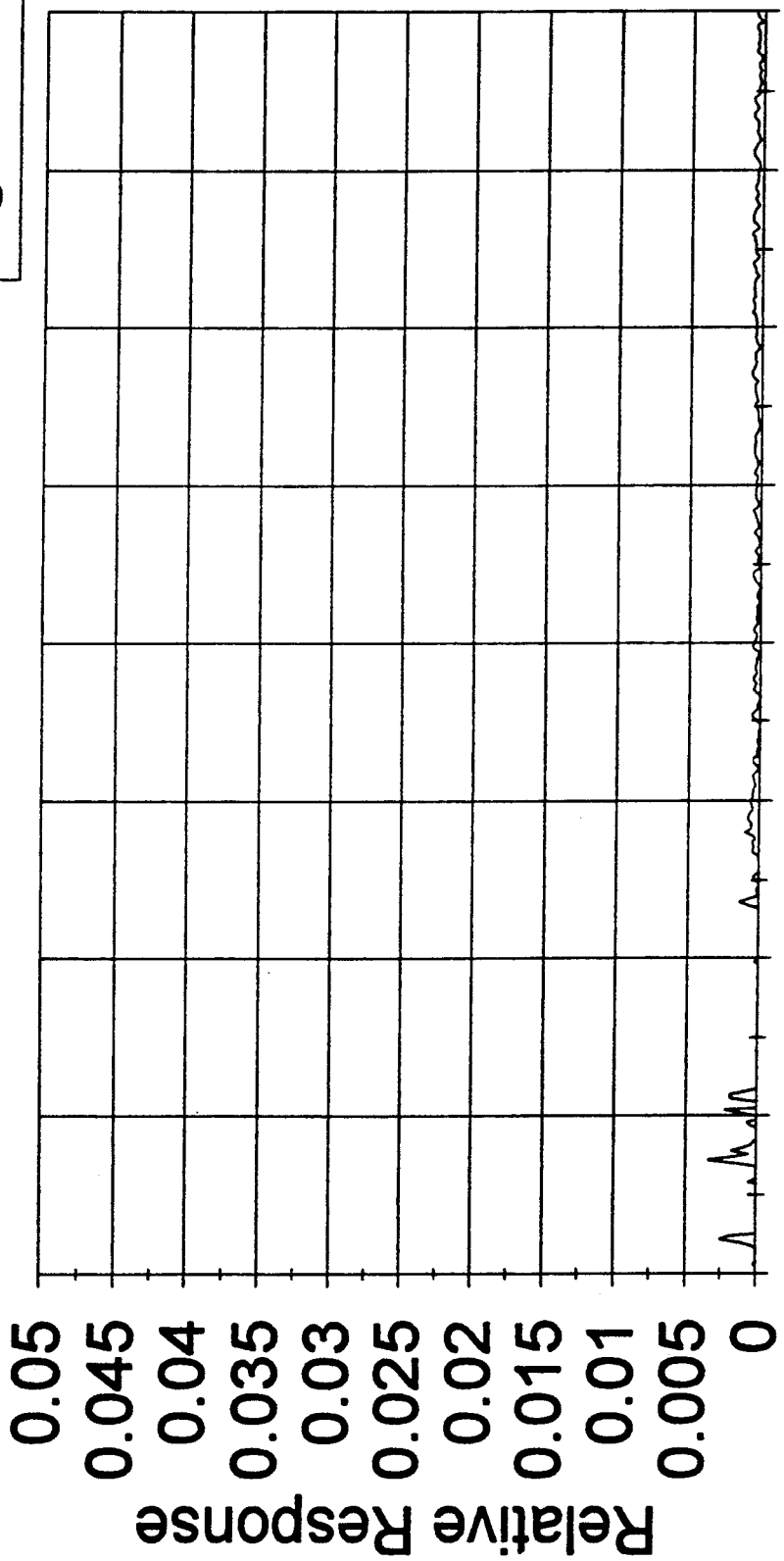
Figure 2E:
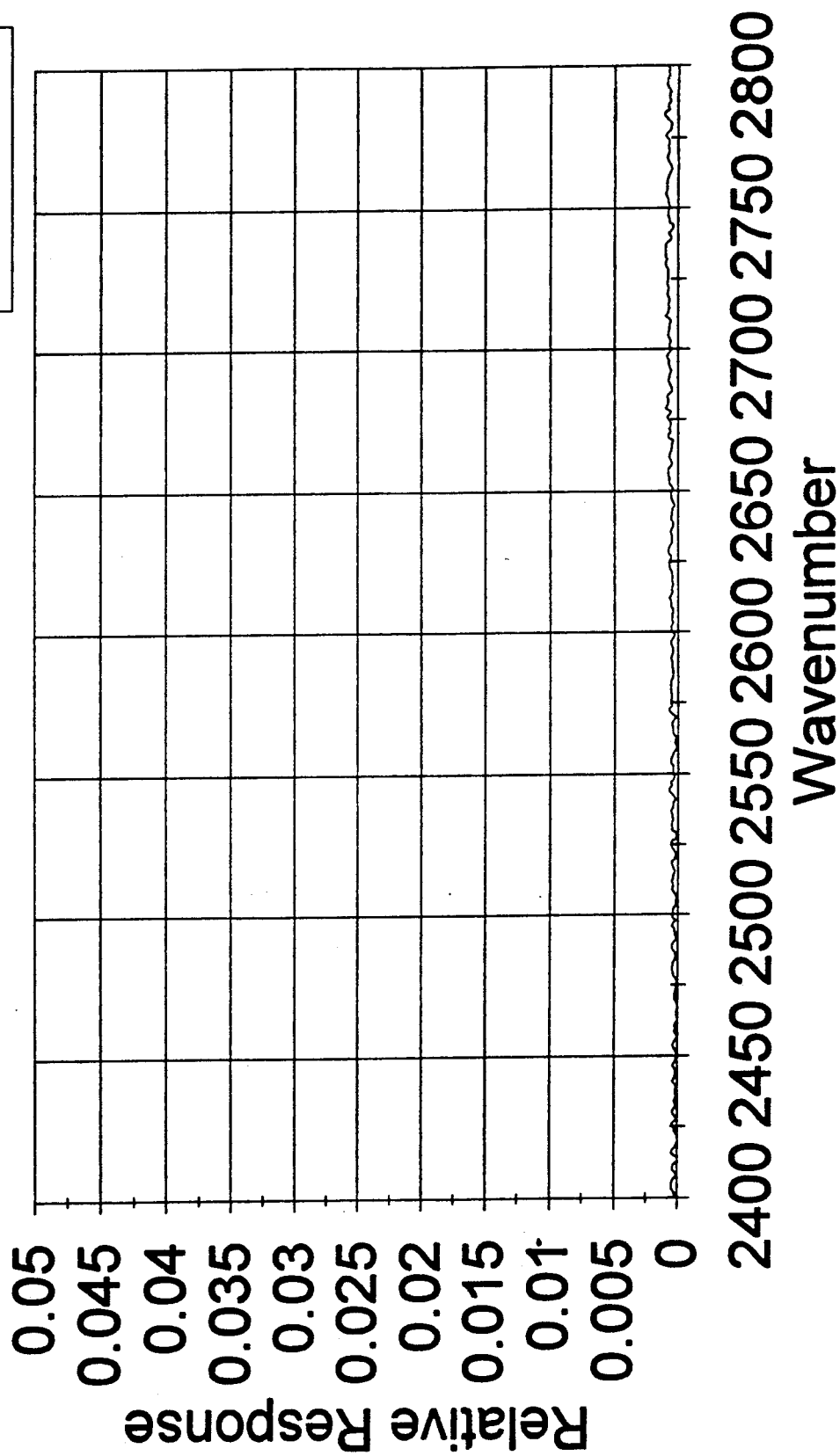
Figure 3F:
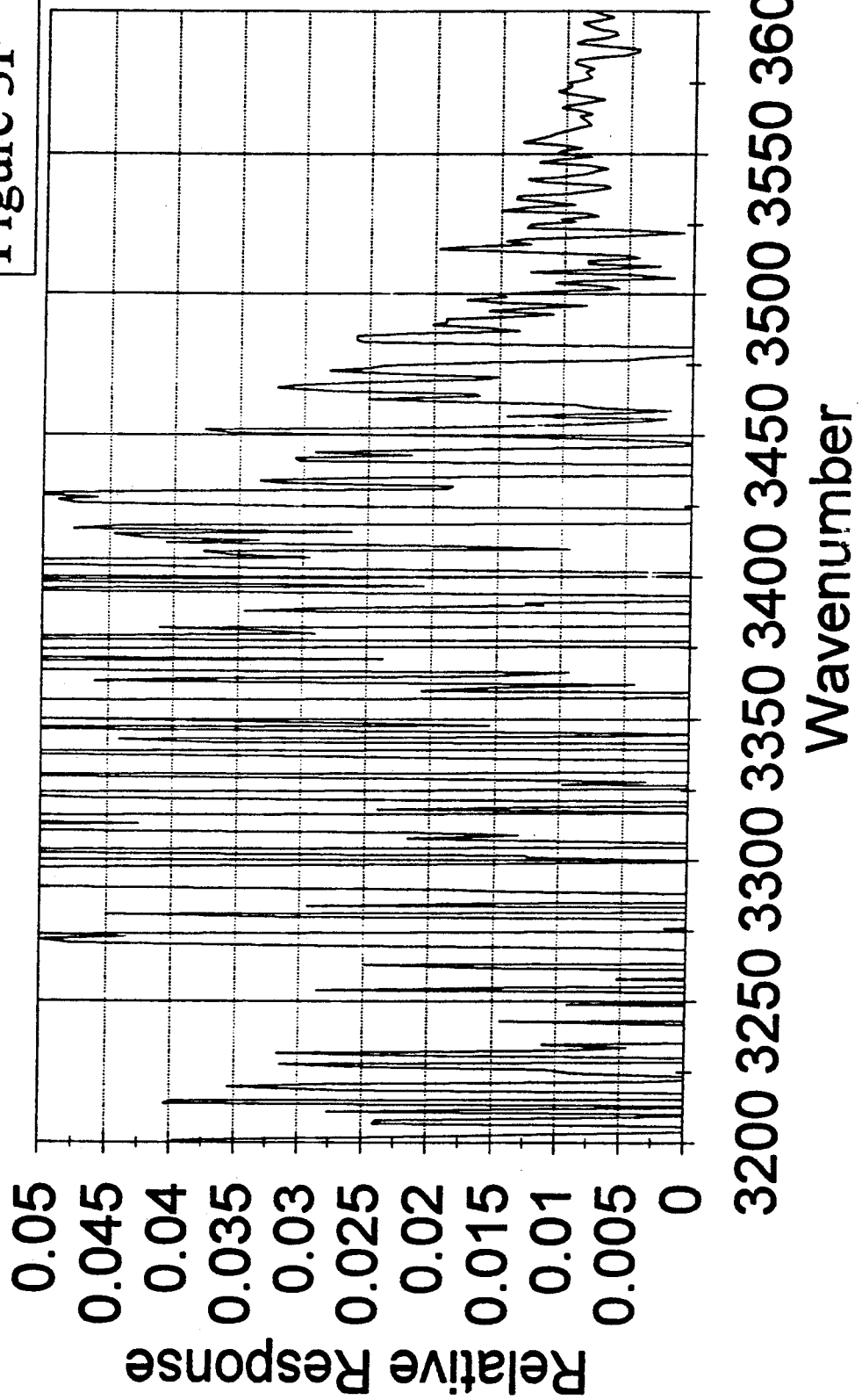
Figure 4D:
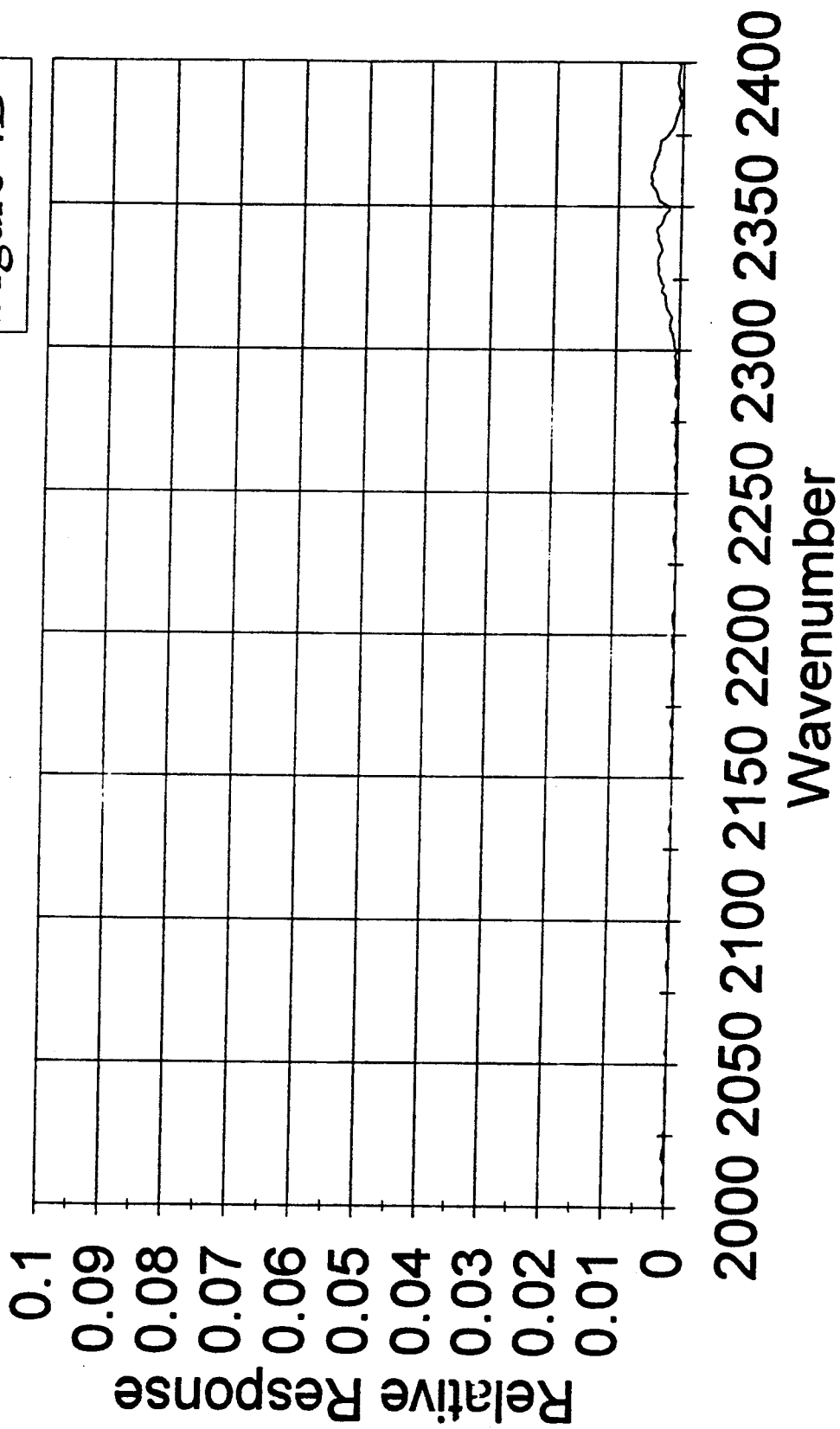
Figure 4H:
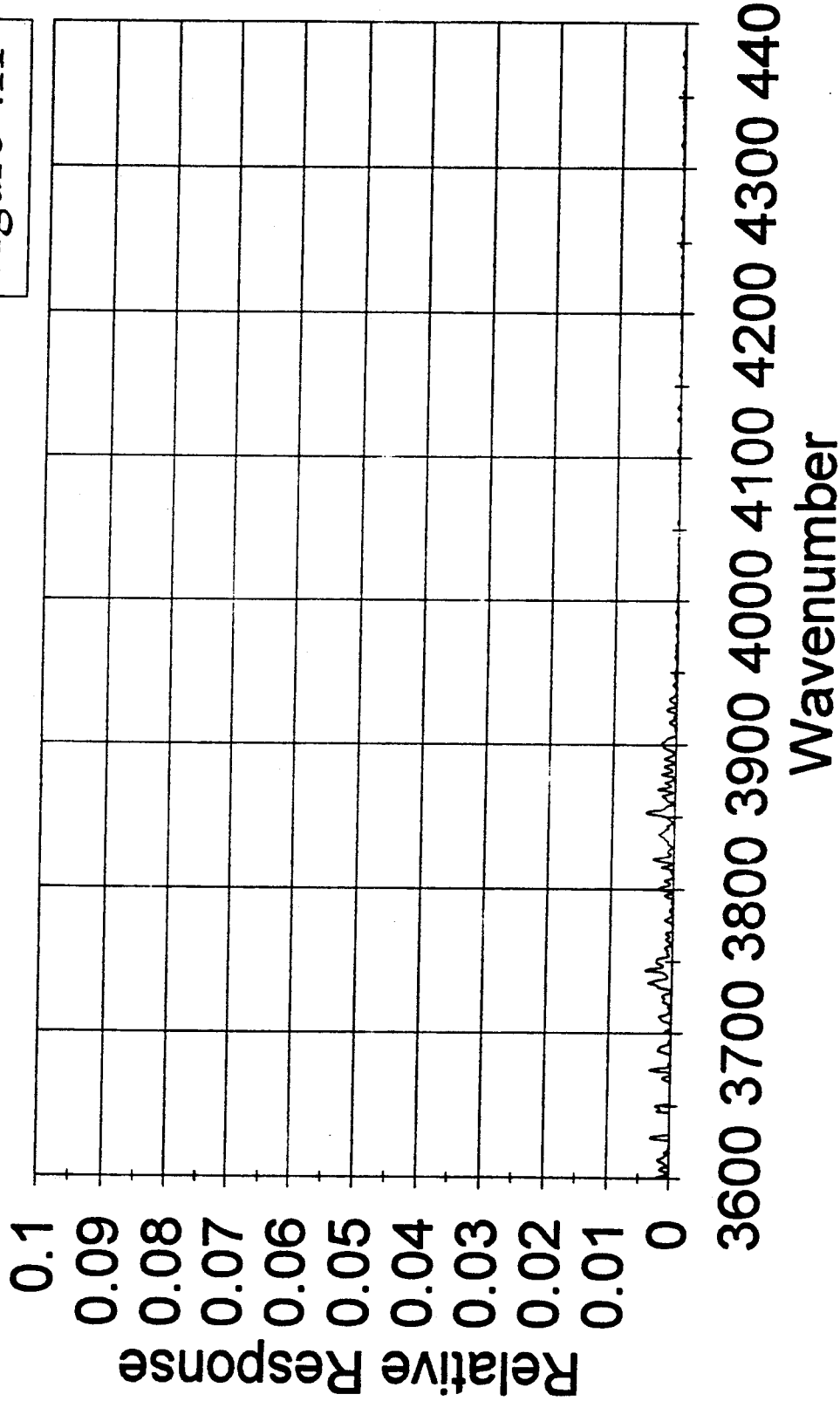

FIG. 1 illustrates a typical biochemical process wherein sucrose is added periodically to sustain the growth of living plant cells in a reactor 11. The sucrose inverts to glucose and fructose and some is consumed by the cells which are undergoing transformation in the process. To maximize the yield of the desired product of the process, in this case cell mass and metabolic by-products, the temperature, pressure and pH of the reaction must be carefully regulated based on the concentration of the sucrose, glucose, and fructose.

A conventional FT-IR instrument 10 (Perkin Elmer Model 1640) is used to obtain absorption spectra on a sample stream from the process. Samples are passed through the transmission cell (not shown) of the FT-IR instrument continuously, with readings taken every 5 to 10 minutes over a period of 72 hours. More frequent readings may be made as required in order to optimize the physical parameters of the process. Conventional monitoring probes 12 are used to monitor the physical parameters of the process and a conventional general purpose computer 14 stores data and provides control functions as required based on the concentration of the reaction ingredients. An output 16 from the FT-IR instrument is connected through an RS-232 port 18 to memory of the computer 14 and the data collected by the FT-IR instrument 10 is stored in the computer's memory.

According to the method of this invention, data files are created which enable the computer 14, based on measurements being made as the process proceeds, to analyze the data and determine the concentration of reactants accurately and rapidly. Based on this determination, the process parameters are adjusted to optimize the process. As discussed above, a digital to analog converter (D/A) 20 is coupled between the computer and a controller 22 which opens and closes a shut off valve 24 for the process. If the sucrose, fructose, and glucose drop below predetermined ranges, more sucrose is added to the system. If they remain high, either pH or temperature is adjusted to increase the rate of cell growth. If unwanted new chemicals are observed as measured by a sudden increase in Chi-square value, the operator is warned. If either the concentrations or physical parameters fall outside dangerous limits for cell viability, the system can be automatically shut down. Temperature, pressure, pH, flow rate are monitored by the conventional sensors or probes 12 and the electronic output measurements are feed to an analog to a digital A/D converter 26 connected between the computer 14 and these probes as discussed above. The output of the A/D converter 26 is connected through an RS-232 port 29. Thus, both the concentration of reactants, and if desired the concentration of the reaction products, are monitored in real time along with the physical parameters of the process to control the process to optimize it. Hitherto this has never been achieved. Consequently, conditions may now be controlled precisely to optimize the process. This has been achieved using this invention for a wide variety of plant and yeast cells.

CREATION OF DATA FILES

In accordance with this invention, calibration samples are prepared before starting the process and data files are created and stored in the memory of the computer 14. The first step of the method of this invention is to prepare a number of calibration samples spanning the concentration range of interest. Ten samples at each concentration were thus prepared. Calibration samples of aqueous solutions of 0.5, 1.0, 3, 5, and 7.0 weight percent sucrose, 0.5, 1, 2, and 4 weight percent glucose, and 0.25, 1, 2, and 4 weight percent fructose were initially prepared and spectra obtained.

The electromagnetic absorption of these calibration samples at a selected number of wavelengths (wavenumbers) over a predetermined range were measured to obtain a spectra for each sample, k values and standard deviations thereof were calculated at each wavenumber, and data files consisting of these values were created and stored in the memory of the computer.

Using one of the following equations:

$$k = \frac{A}{c} \text{ (for gases)} \qquad [9]$$

or $$k = \frac{A - k_{solvent}(1.0 - c)}{c} \qquad [10]$$

(for solvent system - liquids or solids)

A is the absorbance measurement of each individual calibration sample, and
c is the concentration in molar units of the ingredient in the calibration sample,
$k_{solvent}$ is the absorbance value for pure solvent, for example, water, an average k value for each calibration sample is calculated at each of the selected number of different wavelengths over the predetermined range of wavelengths selected. The standard deviation value S of k values were determined according to the following formula.

$$S = \left[ \frac{1}{m-1} \sum_{i=1}^{m} (k_i - \bar{k})^2 \right]^{\frac{1}{2}}$$

where
$k_i$ are the m individual values at each wavenumber,
$\bar{k}$ is the average k at each wavenumber, and
m is the number of replicates performed at each wavenumber (10 for example).

FIGS. 3A-3G is the spectra of the 0.5 weight % glucose-water solution and Table I (Exhibit A) is illustrative of the date file for this solution. FIGS. 2A-2E is the spectra of the 0.25 weight % frutose-water solution and Table II (Exhibit B) is illustrative of the date file for this solution. FIGS. 4A-4H is the spectra of the 3.0% sucrose-water solution and Table III (Exhibit C) is illustrative of the data file for this solution.

In Tables I, II and III, the column designated # presents the wavenumber; the columns designated A through J presents the k values for the ten replicated calibration samples at each wavenumber in the column designated #; the column designated AVG presents the average of the ten k values at each wavenumber; and the column designated STD presents the standard deviation of the average of the ten k values at each wavenumber. Because ten replicated calibration samples were taken for each calibration sample, statistically significant results are obtained. For greater accuracy a greater number of replicas are required. For most purposes twenty replicas are sufficient. The data in the Tables I, II and III is stored as data files in the memory of the computer 14.

After data files for individual reactants have been created, data files for the mixture of reactants is created:

First, a sample mixture of the reactants at known concentrations is prepared and then the electromagnetic absorption of the sample mixture is measured at each of a selected number of different wavelengths over a range of wavelengths of the electromagnetic spectrum anticipated to be best representative of the absorption characteristics of the sample mixture based on collected data from the individual components.

Second, it is determined which wavelengths within the range (scan range) of wavelengths of the electromagnetic spectrum shall provide a solution to the following equations to an acceptable level of precision. This is accomplished by solving the following equations to determine the respective concentrations of the ingredients in the calibration sample mixtures using (i) an arbitrarily selected number of wavelengths within the range of wavelengths, (ii) the lowest standard deviation among the average k values as determined from the data files for the individual calibration samples as set forth in Tables I, II, and III, and (iii) the singular value decomposition mathematical technique to determine which of the arbitrarily selected number of wavelengths (scan range) provide the lowest chi-squared statistic between calculated and known values of the concentration of ingredients in the calibration sample mixtures.

$$A_1 = k_{11}c_1 + k_{12}c_2 + k_{13}c_3 + k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

$$A_n = k_1c_1 + k_2c_2 + k_3c_3 \ldots k_nc_n$$

$$A_m = k_{m1}c_1 + k_{m2}c_2 + k_{m3}c_3 \ldots k_{mn}c_n$$

where
- $A_1, A_2, A_3 \ldots A_n$ are the values of the absorbance measurements at said arbitrarily selected wavelengths,
- $k_{m1}, k_{m2}, k_{m3} \ldots k_{mn}$ are the average k values from the data files for the individual calibration samples which most closely correspond to the k values for the concentration of ingredients in the calibration sample mixtures (the first subscript is the wavenumber and the second matches the subscript for the unknown chemical species being determined), and
- $c_1, c_2, c_3 \ldots c_n$ are the concentrations (either known or unknown) expressed in molar units, of the ingredients in the sample mixtures.

FIGS. 5 and 6 are illustrative of these later steps of the method. FIG. 5 is the spectra over a wavenumber range between 900 and 1150 for a calibration sample mixture of 2.5% sucrose, 0.59% glucose, and 0.30% fructose. Concentrations of ingredients in the calibration samples were determined using k values from the data files of 3% sucrose, 0.5% glucose, and 0.25% fructose aqueous solutions over a scan range of 1114–1032 wavenumber. FIG. 6 is similar to FIG. 5 except for the very important difference that the scan range was 1114–902 wavenumber rather than 1114–1032 wavenumber. Calculated results (dotted line) and actual reading (solid line) from the FT-IR instrument are displayed together. In FIG. 5 the calculated values match more closely to the actual reading than in FIG. 6. Therefore, the scan range of 1114–1032 wavenumber is used to determine unknown concentrations in a sample stream from the process.

ON-LINE MONITORING OF CHEMICAL PROCESS

Using the data files created for the calibration samples and calibration mixture samples, the reactants and products (sucrose, glucose, and fructose) of chemical process shown in FIG. 1 are monitored by measuring the spectra of a sample stream from the process. This spectra is shown in FIG. 7.

First, the chemical process is continually monitored to collect individual samples in which the concentration of ingredients is unknown and the electromagnetic absorption of each individual samples is measured over the scan range which provided the lowest chi-squared statistic between calculated and known values of the concentration of ingredients in the calibration sample mixtures.

Second, the following equations are solved in accordance with singular value decomposition mathematical technique to determine the respective unknown concentrations of the ingredients in the test samples using the average k values at the wavenumbers determined above. Specifically, the following equations are solved at 1114–1032 wavenumbers.

$$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.

.

.

$$A_m = k_{m1}c_1 + k_{m2}c_2 + k_{m3}c_3 + \ldots + k_{mn}c_n$$

where
- $A_1, A_2, A_3 \ldots A_n$ are the values of the absorbance measurements of the test samples (the abscissa of FIG. 7),
- $k_{m1}, k_{m2}, k_{m3} \ldots, k_{mn}$ are the k values from Tables I, II, and III, and
- $c_1, c_2, c_3 \ldots c_n$ are the concentrations expressed in molar units of the unknown ingredients in the test samples, in this case, four values representing sucrose, glucose, fructose, and water.

Forth, the second step is repeated using k values which corresponds most closely to the k value for the concentration of the unknown ingredient as determined in the second step.

Fifth, using the concentration of ingredients as determined in the forth step calculate the absorption of the test sample and compare the calculated absorption with the actual measured absorption. The forth and fifth steps are repeated until the values of k used in determining the unknown concentrations of ingredients in the test samples provide the statistically best results. Specifically, repetition is mandated so that the results obtained in repeated calculations of the unknown concentrations of ingredients in the test samples have a percentage deviation of less than about 1 percent. When this is achieved the concentration of unknown ingredients has been determined with the desired accuracy.

Table IV presents two sets of calculated values for an unknown mixture using the k values for two different mixtures:

TABLE IV (Unknown Sucrose, Glucose, Fructose Solution)

|  | MIXTURE 1 Using k file 3% Suc, 0.5% Glu, .25% Fru | | MIXTURE 2 Using k file 1% Suc, 0.5% Glu, .25% Fru | |
|---|---|---|---|---|
|  | Mass % | Mole % | Mass % | Mole % |
| Sucrose | 1.99 | 0.108 | 2.00 | 0.108 |
| Glucose | 0.48 | 0.049 | 0.45 | 0.046 |
| Fructose | 0.36 | 0.037 | 0.35 | 0.036 |
| Chi-Square Value | 2.3 | | 4.5 | |

In TABLE IV, the MIXTURE 1 comprises 3.0 weight % sucrose, 0.5 weight % glucose, and 0.25 eight % fructose, and MIXTURE 2 comprises 3.0 weight % sucrose, 0.5 weight % glucose, and 0.25% fructose. The results are expressed as mole percent (as mole fractions are used in the calculations) as well as in the more usual engineering units of mass percent. The method of the invention obtained the results using the k files corresponding to mixture two with a Chi-square value of 4.5 and the results using the k files corresponding to mixture 1 with a Chi-square value of 2.5. These were the last two iterations zeroing in on the best values for the unknown concentrations at the desired level of precision (better than 0.1%). The results are taken corresponding to the answers given by the k files associated with mixture 1 because the Chi-square value is lowest.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. (For the purposes of this invention absorbance and transmission and wavelength and wavenumbers are equivalent terms, and light and electromagnetic radiation are equivalent terms.) Consequently, it is not the intention to limit this invention to the particular embodiment disclosed. On the contrary, the intention is to cover all modifications and alternate constructions coming within the spirit and scope of the invention as generally expressed by the following claims:

TABLE I

|  | A | B | C | D | E | F | G | H | I | J | AVG | STD |
|---|---|---|---|---|---|---|---|---|---|---|---|---|
| 1200 | 6.6682 | 6.4678 | 7.3236 | 7.0711 | 7.7343 | 8.4202 | 8.4196 | 8.228 | 9.298 | 9.5587 | 7.91895 | 0.998277 |
| 1199 | 6.071 | 7.0645 | 7.1243 | 7.6678 | 7.5351 | 8.8179 | 9.0163 | 8.8246 | 9.2977 | 9.5584 | 8.09776 | 1.099472 |
| 1198 | 5.8714 | 7.6608 | 7.9197 | 9.458 | 8.3304 | 10.0112 | 9.4136 | 10.0179 | 10.093 | 10.7517 | 8.95277 | 1.409868 |
| 1197 | 5.8713 | 7.2628 | 8.1185 | 9.8558 | 8.7282 | 9.6131 | 8.8166 | 9.8188 | 10.2919 | 11.1495 | 8.95265 | 1.474342 |
| 1196 | 6.2697 | 6.8653 | 7.3231 | 8.6625 | 8.1318 | 9.0167 | 7.8222 | 8.8244 | 10.0934 | 10.1551 | 8.31642 | 1.223374 |
| 1195 | 7.0656 | 7.2632 | 7.522 | 8.4634 | 8.3307 | 9.0166 | 8.2201 | 8.2274 | 10.4913 | 9.9561 | 8.45564 | 1.051619 |
| 1194 | 6.8668 | 7.2634 | 7.7212 | 8.4636 | 8.3309 | 8.0219 | 7.8223 | 8.0286 | 10.0935 | 9.7573 | 8.23695 | 0.957661 |
| 1193 | 6.8667 | 7.2633 | 7.5221 | 8.8614 | 8.3308 | 8.0218 | 8.2202 | 8.4265 | 9.8944 | 9.9562 | 8.33634 | 0.97067 |
| 1192 | 7.8616 | 7.4622 | 8.119 | 9.2594 | 8.3308 | 9.2157 | 8.8171 | 9.4214 | 10.4914 | 10.3541 | 8.93327 | 0.960362 |
| 1191 | 7.8615 | 7.2632 | 7.721 | 9.0603 | 7.9327 | 9.4145 | 8.419 | 10.4162 | 10.2923 | 10.553 | 8.89337 | 1.165092 |
| 1190 | 7.2646 | 7.0643 | 7.3231 | 8.6625 | 7.3359 | 9.0167 | 7.8222 | 10.2173 | 9.4965 | 10.3541 | 8.45572 | 1.201694 |
| 1189 | 6.8666 | 7.2632 | 7.522 | 7.8664 | 7.5348 | 8.6186 | 8.0211 | 9.8192 | 9.8943 | 9.7571 | 8.31633 | 1.079719 |
| 1188 | 6.4689 | 7.0645 | 8.1192 | 7.4688 | 8.132 | 9.0169 | 8.8173 | 9.6205 | 10.2926 | 9.5584 | 8.45591 | 1.160491 |
| 1187 | 6.6677 | 7.4622 | 8.517 | 7.6676 | 8.3308 | 9.4146 | 9.0161 | 9.6203 | 10.2924 | 10.5531 | 8.75418 | 1.195656 |
| 1186 | 7.0659 | 7.6614 | 8.1192 | 7.2698 | 7.734 | 9.4148 | 8.2204 | 9.2226 | 10.2926 | 11.3492 | 8.63499 | 1.326325 |
| 1185 | 6.8672 | 7.2638 | 7.5226 | 7.4691 | 7.5354 | 9.6141 | 8.0217 | 8.6259 | 10.2929 | 10.9516 | 8.41643 | 1.333551 |
| 1184 | 5.674 | 6.6675 | 6.1304 | 6.8728 | 7.5361 | 8.023 | 8.0224 | 8.6266 | 9.6966 | 9.3604 | 7.66098 | 1.270452 |
| 1183 | 5.2762 | 6.4687 | 5.9317 | 6.4751 | 7.1383 | 7.2273 | 7.8236 | 8.8258 | 9.2989 | 9.3606 | 7.38262 | 1.347093 |
| 1182 | 6.0722 | 6.4687 | 6.5286 | 7.072 | 7.1383 | 7.4262 | 7.8236 | 8.8258 | 9.2989 | 9.9576 | 7.66119 | 1.234656 |
| 1181 | 6.868 | 6.0707 | 6.9265 | 7.2709 | 7.5362 | 7.2272 | 7.8235 | 8.4278 | 9.6967 | 9.7585 | 7.7606 | 1.145081 |
| 1180 | 7.0672 | 6.4688 | 7.1256 | 7.0721 | 7.7353 | 6.8294 | 7.6247 | 8.229 | 9.8959 | 9.7587 | 7.78067 | 1.12607 |
| 1179 | 7.4649 | 7.8615 | 7.9214 | 7.4699 | 8.73 | 7.8241 | 8.2215 | 9.2237 | 10.2937 | 10.5544 | 8.55651 | 1.067334 |
| 1178 | 7.2659 | 7.6625 | 8.3193 | 8.0668 | 8.929 | 8.2221 | 9.2164 | 9.2237 | 10.4927 | 11.1513 | 8.85497 | 1.161171 |
| 1177 | 6.8683 | 6.8669 | 8.1206 | 8.0671 | 8.3324 | 7.8244 | 9.4156 | 8.2291 | 10.095 | 10.5547 | 8.43741 | 1.174039 |
| 1176 | 7.6641 | 7.4637 | 7.9216 | 7.868 | 8.3323 | 8.8192 | 9.4155 | 8.8259 | 10.6918 | 10.3556 | 8.73577 | 1.061713 |
| 1175 | 7.8631 | 7.0658 | 7.7226 | 7.868 | 7.5364 | 9.0182 | 9.2166 | 9.4229 | 10.2939 | 9.9577 | 8.59652 | 1.062001 |
| 1174 | 7.4652 | 6.8669 | 7.7227 | 8.0671 | 7.5365 | 8.4213 | 9.2167 | 9.6219 | 10.095 | 9.7588 | 8.47721 | 1.065818 |
| 1173 | 7.6643 | 7.6629 | 8.3197 | 8.8631 | 9.1284 | 9.4163 | 9.2168 | 10.418 | 10.891 | 10.7538 | 9.23343 | 1.113903 |

TABLE II

|  | A | B | C | D | E | F | G | H | I | J | AVG | STD |
|---|---|---|---|---|---|---|---|---|---|---|---|---|
| 1200 | 3.9126 | 1.9748 | 1.3024 | 0.8174 | −0.3395 | −0.9736 | 2.7809 | 2.606 | 1.5901 | 2.4838 | 1.61549 | 1.405705 |
| 1199 | 3.1135 | 1.5752 | 0.1036 | 1.217 | −0.3395 | 0.6247 | 1.9817 | 1.8068 | 0.7909 | 2.0842 | 1.29581 | 0.976847 |
| 1198 | 3.5131 | 1.5752 | −1.0952 | 1.6166 | −0.3395 | 2.2231 | 1.5821 | 1.4072 | 0.7909 | 2.0842 | 1.33577 | 1.237064 |
| 1197 | 5.5104 | 3.5726 | 0.103 | 3.2143 | 1.6578 | 4.2204 | 2.7803 | 0.6074 | 2.3886 | 4.0816 | 2.81364 | 1.591495 |
| 1196 | 7.5079 | 6.3693 | 2.8997 | 6.011 | 4.4545 | 6.2179 | 4.3782 | 1.8058 | 4.3862 | 5.6795 | 4.971 | 1.637021 |
| 1195 | 6.7089 | 6.3694 | 3.699 | 7.2099 | 4.4546 | 5.4189 | 4.7779 | 4.603 | 5.9846 | 5.6796 | 5.49058 | 1.052442 |
| 1194 | 5.5107 | 5.1712 | 3.6996 | 5.6122 | 3.2565 | 4.6203 | 4.7785 | 5.4028 | 5.186 | 6.0798 | 4.93176 | 0.830977 |
| 1193 | 5.1116 | 3.1738 | 2.5013 | 2.8155 | 1.259 | 3.0224 | 3.9798 | 3.0058 | 2.3894 | 5.2811 | 3.25397 | 1.170242 |
| 1192 | 5.5115 | 1.5757 | 1.7024 | 1.6171 | 2.4581 | 2.6232 | 3.181 | 2.2069 | 2.7893 | 4.8819 | 2.85471 | 1.280808 |
| 1191 | 5.1116 | 3.5734 | 2.1017 | 2.416 | 3.257 | 3.422 | 2.7811 | 3.0058 | 4.787 | 4.482 | 3.49376 | 0.958093 |

TABLE II-continued

|      | A      | B      | C      | D      | E      | F      | G      | H      | I      | J      | AVG     | STD      |
|------|--------|--------|--------|--------|--------|--------|--------|--------|--------|--------|---------|----------|
| 1190 | 4.7117 | 4.7718 | 2.9006 | 3.2148 | 3.6563 | 3.8213 | 3.9795 | 4.2042 | 6.385  | 4.0821 | 4.17273 | 0.922833 |
| 1189 | 4.7115 | 3.9725 | 2.9004 | 3.2146 | 4.8548 | 3.8211 | 4.7785 | 4.204  | 5.9852 | 4.0819 | 4.25245 | 0.839866 |
| 1188 | 5.9105 | 4.7718 | 4.0994 | 4.014  | 4.855  | 5.0201 | 5.5779 | 3.8046 | 5.5858 | 6.4796 | 5.01187 | 0.835447 |
| 1187 | 5.9106 | 6.7699 | 3.6999 | 5.2129 | 5.2547 | 5.8194 | 5.9776 | 4.2043 | 4.7868 | 7.2789 | 5.4915  | 1.041421 |
| 1186 | 4.712  | 7.5693 | 4.0997 | 5.2131 | 6.0541 | 6.2191 | 5.1786 | 5.0037 | 4.3874 | 6.0803 | 5.45173 | 0.983421 |
| 1185 | 6.3103 | 6.77   | 4.8987 | 5.213  | 5.2548 | 6.219  | 4.3793 | 6.6019 | 5.1864 | 4.8815 | 5.57149 | 0.786793 |
| 1184 | 6.3106 | 6.3707 | 4.0999 | 4.0145 | 4.4559 | 5.8198 | 3.5804 | 6.6022 | 5.1867 | 4.0826 | 5.05233 | 1.085237 |
| 1183 | 3.9136 | 4.7729 | 2.5021 | 2.0172 | 3.6574 | 3.4228 | 2.7819 | 1.8078 | 3.589  | 3.6836 | 3.21483 | 0.873166 |
| 1182 | 4.7129 | 4.773  | 3.3014 | 2.8164 | 4.057  | 4.2221 | 2.782  | 1.0087 | 4.3883 | 4.4829 | 3.65447 | 1.125555 |
| 1181 | 6.7103 | 5.5716 | 4.1    | 5.613  | 4.8556 | 6.2194 | 3.9801 | 4.2048 | 5.5864 | 5.681  | 5.25222 | 0.882577 |
| 1180 | 7.1096 | 4.7722 | 4.0998 | 6.0123 | 5.255  | 6.6188 | 5.9779 | 6.2026 | 5.5862 | 6.0804 | 5.77148 | 0.835737 |
| 1179 | 6.7105 | 4.3731 | 3.7006 | 4.4144 | 4.4562 | 4.6213 | 4.3799 | 6.203  | 5.5866 | 4.8821 | 4.93277 | 0.890722 |
| 1178 | 5.9118 | 5.1727 | 3.7011 | 3.2161 | 2.8584 | 3.8226 | 3.5812 | 5.8039 | 5.5871 | 4.0834 | 4.37383 | 1.078266 |
| 1177 | 5.1125 | 4.773  | 3.701  | 4.0152 | 4.057  | 5.0213 | 3.9807 | 4.2054 | 6.3862 | 4.4829 | 4.57352 | 0.751769 |
| 1176 | 5.5119 | 4.3733 | 4.5    | 4.8142 | 5.6552 | 5.8203 | 4.7797 | 2.6069 | 6.386  | 4.8823 | 4.93298 | 0.985235 |
| 1175 | 5.1125 | 4.3735 | 3.701  | 4.0152 | 3.2579 | 5.0213 | 5.1795 | 2.6071 | 4.7879 | 5.282  | 4.33379 | 0.868453 |
| 1174 | 3.914  | 3.175  | 2.9021 | 2.0176 | 1.6598 | 3.4232 | 3.5814 | 2.6074 | 2.7902 | 3.2844 | 2.93551 | 0.662678 |
| 1173 | 4.3139 | 1.1774 | 2.5028 | 1.6183 | 0.8609 | 2.6244 | 1.9834 | 3.4068 | 2.3909 | 2.8851 | 2.37639 | 0.980592 |

TABLE III

|      | A      | B      | C      | D      | E      | F      | G      | H      | I      | J      | AVG     | STD      |
|------|--------|--------|--------|--------|--------|--------|--------|--------|--------|--------|---------|----------|
| 1200 | 5.1353 | 4.8723 | 4.4502 | 4.6972 | 4.6605 | 4.2316 | 4.3961 | 4.6604 | 4.1895 | 4.1641 | 4.54572 | 0.301038 |
| 1199 | 4.7661 | 4.6262 | 4.2658 | 4.328  | 4.1681 | 4.0471 | 4.2116 | 4.0449 | 4.1898 | 3.9797 | 4.26273 | 0.240997 |
| 1198 | 4.5814 | 4.5647 | 4.2659 | 3.9586 | 4.1066 | 3.7393 | 3.9038 | 3.7371 | 4.0052 | 3.795  | 4.06576 | 0.29763  |
| 1197 | 4.5813 | 4.4415 | 4.2042 | 3.7738 | 4.1681 | 3.4929 | 3.5958 | 3.6754 | 3.8203 | 3.7333 | 3.94866 | 0.354529 |
| 1196 | 4.4584 | 4.257  | 4.0198 | 3.7741 | 4.0452 | 3.3084 | 3.4114 | 3.6757 | 3.5743 | 3.3642 | 3.78885 | 0.374058 |
| 1195 | 4.643  | 4.3184 | 4.0196 | 3.9586 | 4.1682 | 3.5546 | 3.4727 | 3.8602 | 3.6357 | 3.2408 | 3.88718 | 0.402865 |
| 1194 | 4.9507 | 4.5645 | 4.512  | 4.3279 | 4.4759 | 4.1086 | 3.842  | 4.1064 | 3.8818 | 3.4869 | 4.22567 | 0.404313 |
| 1193 | 4.7045 | 4.4415 | 4.7585 | 4.3896 | 4.3529 | 4.2319 | 4.0269 | 3.9833 | 3.9435 | 3.7333 | 4.25659 | 0.318372 |
| 1192 | 4.6434 | 4.2572 | 4.5742 | 4.1438 | 3.9839 | 3.9245 | 3.7811 | 3.7991 | 3.944  | 3.9186 | 4.09698 | 0.289905 |
| 1191 | 4.7663 | 4.4417 | 4.5739 | 4.2667 | 3.922  | 4.0473 | 3.9039 | 3.9219 | 4.0053 | 4.2262 | 4.20752 | 0.287578 |
| 1190 | 4.5816 | 4.6265 | 4.6356 | 4.2668 | 3.9221 | 4.2322 | 3.9656 | 3.7989 | 3.8822 | 4.1647 | 4.20762 | 0.3029   |
| 1189 | 4.4586 | 4.5651 | 4.5126 | 3.959  | 3.9839 | 4.1092 | 4.1506 | 3.6143 | 3.8824 | 3.857  | 4.10927 | 0.298764 |
| 1188 | 4.5819 | 4.3189 | 4.328  | 3.9551 | 4.1687 | 4.0477 | 4.0891 | 3.7992 | 4.0057 | 3.7955 | 4.10938 | 0.234685 |
| 1187 | 4.3973 | 4.1343 | 4.1433 | 4.144  | 4.0456 | 3.8631 | 3.7813 | 3.6761 | 3.7594 | 3.7956 | 3.974   | 0.219915 |
| 1186 | 4.3974 | 4.3807 | 4.2666 | 4.3904 | 3.9226 | 3.9864 | 4.0277 | 3.6762 | 3.8827 | 3.9189 | 4.08496 | 0.242134 |
| 1185 | 4.3358 | 4.627  | 4.5129 | 4.5136 | 3.9842 | 4.1095 | 4.0277 | 3.7378 | 4.0059 | 3.8573 | 4.17117 | 0.290156 |
| 1184 | 4.3361 | 4.381  | 4.4516 | 4.3291 | 4.1076 | 3.9867 | 3.7817 | 3.7997 | 3.883  | 3.796  | 4.08525 | 0.255447 |
| 1183 | 4.6439 | 4.1961 | 4.1436 | 4.0211 | 4.1075 | 3.8634 | 3.9047 | 3.9227 | 3.575  | 3.8575 | 4.02355 | 0.267355 |
| 1182 | 4.5824 | 4.3194 | 3.959  | 3.8365 | 3.8613 | 3.8635 | 3.7817 | 3.8612 | 3.3288 | 3.796  | 3.91898 | 0.316369 |
| 1181 | 4.2131 | 4.3196 | 3.8976 | 3.9598 | 3.5536 | 3.8021 | 3.6587 | 3.7383 | 3.2674 | 3.7962 | 3.82064 | 0.289759 |
| 1180 | 4.3365 | 4.3814 | 3.9594 | 4.2064 | 3.6154 | 3.8639 | 3.9052 | 3.9848 | 3.5139 | 3.6733 | 3.94402 | 0.281122 |
| 1179 | 4.4598 | 4.32   | 4.0827 | 4.2066 | 3.8619 | 3.8025 | 4.0286 | 3.985  | 3.6989 | 3.6119 | 4.00579 | 0.257567 |
| 1178 | 4.46   | 4.2586 | 4.2061 | 4.0836 | 4.0468 | 3.9875 | 4.0288 | 3.862  | 3.8222 | 3.7352 | 4.04908 | 0.206834 |
| 1177 | 4.6449 | 4.3203 | 4.391  | 4.0837 | 4.2317 | 4.1723 | 4.0905 | 3.9853 | 4.0071 | 3.6738 | 4.16006 | 0.249082 |
| 1176 | 4.8914 | 4.3821 | 4.4527 | 4.3918 | 4.4166 | 4.0493 | 4.2754 | 4.0471 | 4.1304 | 3.674  | 4.27108 | 0.306843 |
| 1175 | 5.0764 | 4.6286 | 4.5761 | 4.6384 | 4.54   | 4.0495 | 4.3372 | 4.1705 | 4.1306 | 4.0437 | 4.4191  | 0.31505  |
| 1174 | 5.3264 | 5.0596 | 4.8223 | 4.9462 | 4.8478 | 4.4189 | 4.4603 | 4.4783 | 4.3153 | 4.5362 | 4.72075 | 0.311529 |
| 1173 | 5.7535 | 5.4289 | 5.1916 | 5.3155 | 5.2787 | 4.9114 | 4.8296 | 4.9707 | 4.6846 | 4.9055 | 5.127   | 0.308302 |

Using a general purpose computer and an electromagnetic absorption or reflection instrument, a method of determining the respective concentrations of a plurality of different ingredients present in a chemical process, comprising
(I) first creating data files by
  (a) preparing a number of calibration samples at different concentrations spanning the concentration range of interest for each individual ingredient being monitored,
  (b) measuring the electromagnetic absorption of the calibration samples at a selected number of different wavelengths over a predetermined range of wavelengths of the electromagnetic spectrum and storing the measurements in a data file in the memory of the computer,
  (c) repeating steps (a) and (b) a sufficient number of times to obtain statistically significant data composed of these absorbance measurements for the known concentrations of each of the ingredients and storing said data in a data file in the memory of the computer,
  (d) using the following equations $$k = \frac{A}{c}$$
(for gases)

or $$k = \frac{A - k_{solvent}(1.0 - c)}{c}$$
(for solvent system - liquids or solids)

where
A is the absorbance measurement of each individual calibration sample, and
c is the concentration in molar units of the ingredient in the calibration sample,
$k_{solvent}$ (for liquids and solids) is the absorbance value of the component designated as a solvent in which the other components are distributed measured in its pure form,
calculating for each calibration sample an average k value at each of said selected number of different wavelengths over said predetermined range of wavelengths, and a standard deviation value thereof, and storing said calculated k values and standard deviation values thereof in a data file in the memory of the computer, (e) preparing a plurality of calibration sample mixtures of the ingredients at known concentrations and measuring the electromagnetic absorption of the calibration sample mixtures at each wavelength within said range of wavelengths of the electromagnetic spectrum, (f) determining which wavelength within said range of wavelengths of the electromagnetic spectrum shall provide a solution to the following equations to an acceptable level of precision by solving said following equations to determine the respective concentrations of the ingredients in the calibration sample mixtures using (i) an arbitrarily selected number of wavelengths within said range of wavelengths, (ii) the lowest standard deviation among the average k values as determined in step (d), and (iii) the singular value decomposition mathematical technique to determine which of the arbitrarily selected number of wavelengths provide the lowest chi-squared statistic between calculated and known values of the concentration of ingredients in the calibration sample mixtures $$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.

.

.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements at said arbitrarily selected wavelengths, $k_{m1}, k_{m2}, k_{m3} \ldots k_n$ are the average k values from step (d) which most closely correspond to the k values for the concentration of ingredients in the calibration sample mixtures for each wavenumber or wavelength, and $c_1, c_2, c_3 \ldots c_n$ are the concentrations(either known or unknown) expressed in molar units, of the ingredients in the sample mixtures, (II) second conducting on-line monitoring of the chemical process by (i) continually sampling the chemical process to collect individual samples in which the concentration of ingredients is unknown and measuring the electromagnetic absorption of said individual samples at the arbitrarily selected number of wavelengths which provide the lowest chi-squared statistic between calculated and known values of the concentration of ingredients in the calibration sample mixtures as determined in step (f), (j) solving the following equations in accordance with singular value decomposition mathematical technique to determine the respective unknown concentrations of the ingredients in the samples taken in step (i) using the average k values at the wave lengths determined in step (f)

$$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.

.

.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements taken in step (i), $k_{m1}, k_{m2}, k_{m3} \ldots, k_n$ are the k values from step (d) at each wavenumber or wavelength n, and $c_1, c_2, c_3 \ldots c_n$ are the concentrations expressed in molar units of the unknown ingredients in the samples, (k) repeating step (j) using k values which corresponds most closely to the k value for the concentration of the unknown ingredient as determined in step (j), (l) using the concentration of ingredients as determined in step (k), calculating absorption of the unknown sample and comparing said calculated absorption with the actual measured absorption, and (m) repeating steps (k) and (l) until the statistically best values of k used in determining the concentrations of unknown ingredients so that the results obtained in repeated calculations of the unknown concentrations of ingredients in the samples have a percentage deviation of less than about 1 percent.

I claim:

1. Using a general purpose computer having memory and an electromagnetic spectrum analysis instrument, a method of determining the concentrations of a plurality of different ingredients present over a concentration range in a chemical process, comprising (I) first creating data files in the computer memory by (a) preparing a number of calibration samples at different concentrations spanning said concentration range for each individual ingredient being monitored, (b) measuring the electromagnetic absorption of the calibration samples at a selected number of different wavelengths over a predetermined range of wavelengths of the electromagnetic spectrum and storing the measurements in a first data file in the memory of the computer, (c) repeating steps (a) and (b) a sufficient number of times to obtain statistically significant data composed of these absorbance measurements for the known concentrations of each of the ingredients and storing said data in a second data file in the memory of the computer, (d) using the computer, the data in said first and second data files, and the following equations $$k = \frac{A}{c}$$

(for gases)

-continued or $$k = \frac{A - k_{solvent}(1.0 - c)}{c}$$

(for solvent system - liquids or solids)

where

A is the absorbance measurement of each individual calibration sample, and c is the concentration in molar units of the ingredient in the calibration sample, $k_{solvent}$ (for liquids and solids) is the absorbance value of the component designated as a solvent in which the other components are distributed measured in its pure form, calculating for each calibration sample an average k value at each of said selected number of different wavelengths over said predetermined range of wavelengths, and a standard deviation value thereof, and storing said calculated k values and standard deviation values thereof in a third data file in the memory of the computer, (e) preparing a plurality of calibration sample mixtures of the ingredients at known concentrations and measuring the electromagnetic absorption of the calibration sample mixtures at each wavelength within said range of wavelengths of the electromagnetic spectrum, (f) using the computer and the data in said third data file determining which wavelength within said range of wavelengths of the electromagnetic spectrum shall provide a solution to the following equations to an acceptable level of precision by solving said following equations to determine the respective concentrations of the ingredients in the calibration sample mixtures using (i) an arbitrarily selected number of wavelengths within said range of wavelengths, (ii) the lowest standard deviation among the average k values as determined in step (d), and (iii) the singular value decomposition mathematical technique to determine which of the arbitrarily selected number of wavelengths provide the lowest chi-squared statistic between calculated and known values of the concentration of ingredients in the calibration sample mixtures $A_1 = k_{11}c_1 + k_{12}c_2 + k_{13}c_3 \ldots k_{1n}c_n$ $A_2 = k_{21}c_1 + k_{22}c_2 + k_{23}c_3 \ldots k_{2n}c_n$ $A_3 = k_{31}c_1 + k_{32}c_2 + k_{33}c_3 \ldots k_{3n}c_n$

.

.

.

$A_m = k_{m1}c_1 + k_{m2}c_2 + k_{m3}c_3 + \ldots + k_{mn}c_n$ where $A_1, A_2, A_3 \ldots A_n$ are the values of the absorbance measurements at said arbitrarily selected wavelengths, $k_{m1}, k_{m2}, k_{m3} \ldots k_n$ are the average k values from step (d) which most closely correspond to the k values for the concentration of ingredients in the calibration sample mixtures for each wavenumber or wavelength, and $c_1, c_2, c_3 \ldots c_n$ are the concentrations (either known or unknown) expressed in molar units, of the ingredients in the sample mixtures, (II) second conducting on-line monitoring of the chemical process by (i) continually sampling the chemical process to collect individual samples in which the concentration of ingredients is unknown and measuring the electromagnetic absorption of said individual samples at the arbitrarily selected number of wavelengths which provide the lowest chi-squared statistic between calculated and known values of the concentration of ingredients in the calibration sample mixtures as determined in step (f), (j) using the computer solving the following equations using the singular value decomposition mathematical technique to determine the respective unknown concentrations of the ingredients in the samples taken in step (i) using the average k values at the wave lengths determined in step (f)

$A_1 = k_{11}c_1 + k_{12}c_2 + k_{13}c_3 \ldots k_{1n}c_n$ $A_2 = k_{21}c_1 + k_{22}c_2 + k_{23}c_3 \ldots k_{2n}c_n$ $A_3 = k_{31}c_1 + k_{32}c_2 + k_{33}c_3 \ldots k_{3n}c_n$

.

.

.

$A_m = k_{m1}c_1 + k_{m2}c_2 + k_{m3}c_3 + \ldots + k_{mn}c_n$ where $A_1, A_2, A_3 \ldots A_n$ are the values of the absorbance measurements taken in step (i), $k_{m1}, k_{m2}, k_{m3} \ldots k_n$ are the k values from step (d) at each wavenumber or wavelength n, and $c_1, c_2, c_3 \ldots c_n$ are the concentrations expressed in molar units of the unknown ingredients in the samples, (k) repeating step (j) using k values which corresponds most closely to the k value for the concentration of the unknown ingredient as determined in step (j), (l) using the concentration of ingredients as determined in step (k), calculating using the computer absorption of the unknown sample and comparing said calculated absorption with the actual measured absorption, and (m) repeating steps (k) and )l) until the statistically best values of k used in determining the concentrations of unknown ingredients so that the results obtained in repeated calculations of the unknown concentrations of ingredients in the samples have a percentage deviation of less than about 1 percent.

2. Based on real time measurements, an on-line method of controlling a chemical process producing an effluent stream in which a plurality of ingredients are present at different concentrations over a concentration range depending on predetermined variable conditions occurring in the process, said method comprising monitoring the concentrations of the ingredients present in said effluent stream, and altering said process conditions as determined by absorption data of the effluent stream taken with an electromagnetic absorption instrument and using a general purpose computer having memory to adjust control device that regulate said process conditions to produce a desired concentration of ingredients in the effluent stream, said absorption data reflecting essentially accurately the concentration of the ingredients in the effluent stream as determined by a method, comprising (I) first creating data files in the computer memory by (a) preparing a number of calibration samples at different concentrations spanning said concentration range for each individual ingredient being monitored, (b) measuring the electromagnetic absorption of the calibration samples at a selected number of different wavelengths over a predetermined range of wavelengths of the electromagnetic spectrum and storing the measurements in a first data file in the memory of the computer, (c) repeating steps (a) and (b) a sufficient number of times to obtain statistically significant data composed of these absorbance measurements for the known concentrations of each of the ingredients and storing said data in a second data file in the memory of the computer, (d) using the computer, the data in said first and second data files, and the following equations $$k = \frac{A}{c}$$
(for gases)

or $$k = \frac{A - k_{solvent}(1.0 - c)}{c}$$
(for solvent system - liquids or solids)

where

A is the absorbance measurement of each individual calibration sample, and c is the concentration in molar units of the ingredient in the calibration sample, $k_{solvent}$ (for liquids and solids) is the absorbance value of the component designated as a solvent in which the other components are distributed measured in its pure form, calculating for each calibration sample an average k value at each of said selected number of different wavelengths over said predetermined range of wavelengths, and a standard deviation value thereof, and storing said calculated k values and standard deviation values thereof in a third data file in the memory of the computer, (e) preparing a plurality of calibration sample mixtures of the ingredients at known concentrations and measuring the electromagnetic absorption of the calibration sample mixtures at each wavelength within said range of wavelengths of the electromagnetic spectrum, (f) using the computer and the data in said third data file determining which wavelength within said range of wavelengths of the electromagnetic spectrum shall provide a solution to the following equations to an acceptable level of precision by solving said following equations to determine the respective concentrations of the ingredients in the calibration sample mixtures using (i) an arbitrarily selected number of wavelengths within said range of wavelengths, (ii) the lowest standard deviation among the average k values as determined in step (d), and (iii) the singular value decomposition mathematical techniques to determine which of the arbitrarily selected number of wavelengths provide the lowest chi-square statistic between calculated and known values of the concentration of ingredients in the calibration sample mixtures $$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.
.
.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements at said arbitrarily selected wavelengths, $k_{m1}, k_{m2}, k_{m3} \ldots k_n$ are the average k values from step (d) which most closely correspond to the k values for the concentration of ingredients in the calibration sample mixtures for each wavenumber or wavelength, and $c_1, c_2, c_3 \ldots c_n$ are the concentrations (either known or unknown) expressed in molar units, of the ingredients in the sample mixtures, (II) second conducting on-line monitoring of the chemical process by (i) continually sampling the chemical process to collect individual samples in which the concentration of ingredients is unknown and measuring the electromagnetic absorption of said individual samples at the arbitrarily selected number of wavelengths which provide the lowest chi-squared statistic between calculated and known values of the concentration of ingredients in the calibration sample mixtures as determined in step (f), (j) using the computer solving the following equations using the singular value decomposition mathematical technique to determine the respective unknown concentrations of the ingredients in the samples taken in step (i) using the average k values at the wave lengths determined in step (f)

$$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.
.
.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements taken in step (i), $k_{m1}, k_{m2}, k_{m3} \ldots k_n$ are the k values from step (d) at each wavenumber or wavelength n, and $c_1, c_2, c_3 \ldots c_n$ are the concentrations expressed in molar units of the unknown ingredients in the samples, (k) repeating step (j) using k values which corresponds most closely to the k value for the concentration of the unknown ingredient as determined in step (j), (l) using the concentration of ingredients as determined in step (k), calculating using the computer absorption of the unknown sample and comparing said calculated absorption with the actual measured absorption, and (m) repeating steps (k) and (l) until the statistically best values of k used in determining the concentrations of unknown ingredients so that the results obtained in repeated calculations of the unknown concentrations of ingredients in the samples have a percentage deviation of less than about 1 percent.

3. An on-line method of monitoring and controlling a chemical process having physical parameters and where the concentration of process components is measured, comprising (a) measuring the concentration of process components in samples from the process using a spectrometric instrument to obtain spectral data characteristic of the process components, (b) analyzing the spectral data using a chi-squared mathematical technique to determine the unknown concentration of process components in said samples, and (c) monitoring the physical parameters of the process and altering said physical parameters based on the determination of concentration of process components in step (b) as required to optimize the process.

* * * * *

UNITED STATES PATENT AND TRADEMARK OFFICE
CERTIFICATE OF CORRECTION

PATENT NO. : 5,262,961
DATED : November 16, 1993
INVENTOR(S) : William A. Farone It is certified that error appears in the above-indentified patent and that said Letters Patent is hereby corrected as shown below:

Column 6, line 25, change "$cm^1$" to --$cm^{-1}$--
Column 6, line 45, change "process repeated" to --process is repeated--
Column 7, line 22, change "k s determined form knowns" to --k's determined form known--
Column 7, line 46, change "use" to --used--
Column 7, line 61, change "on board" to --on-board--

In the DESCRIPTION OF THE DRAWING

Column 8, line 46, change "4H the" to --4H is the--

In the DESCRIPTION OF THE PREFERRED EMBODIMENT

Column 9, line 59, change "feed" to --fed--

Column 10, line 47 and 48, change $(k_i - k)^2$ to --$(k_i - \bar{k})^2$

UNITED STATES PATENT AND TRADEMARK OFFICE
CERTIFICATE OF CORRECTION

PATENT NO. : 5,262,961
DATED : November 16, 1993
INVENTOR(S) : William A. Farone Page 2 of 2

It is certified that error appears in the above-indentified patent and that said Letters Patent is hereby corrected as shown below:

```
Column 12, line 60, change "Forth" to --Fourth--
Column 12, line 65, change "forth" to --fourth--
Column 12, line 67, change "forth" to --foruth--

Column 15, lines 47 through 68, delete
Column 16, lines 47 through 68, delete
(NOTE:  Table II and Table III should be left as is)

Column 17, lines 1 through 68, delete
Column 18, lines 1 through 39, delete
(NOTE:  Should start with "I claim:")

In the CLAIMS

Column 20, line 22, change "wave lengths" to --wavelengths--
Column 20, line 54, change ")1)" to --(1)--
Column 21, line 7, change "device" to --devices--
```

Signed and Sealed this

Nineteenth Day of July, 1994

Attest:

BRUCE LEHMAN

Attesting Officer

Commissioner of Patents and Trademarks